US008067573B2

(12) United States Patent
Hochberg et al.

(10) Patent No.: US 8,067,573 B2
(45) Date of Patent: Nov. 29, 2011

(54) NUCLEIC ACID AGENTS FOR DOWNREGULATING H19 AND METHODS OF USING SAME

(75) Inventors: Avraham Hochberg, Jerusalem (IL); Imad Matouk, East Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 199 days.

(21) Appl. No.: 11/994,810

(22) PCT Filed: Jul. 6, 2006

(86) PCT No.: PCT/IL2006/000785
§ 371 (c)(1),
(2), (4) Date: Jul. 8, 2008

(87) PCT Pub. No.: WO2007/007317
PCT Pub. Date: Jan. 18, 2007

(65) Prior Publication Data
US 2009/0143321 A1    Jun. 4, 2009

Related U.S. Application Data

(60) Provisional application No. 60/696,795, filed on Jul. 7, 2005.

(51) Int. Cl.
*C07H 21/04* (2006.01)
(52) U.S. Cl. .......... 536/24.5; 536/24.1; 536/24.31; 435/6; 435/325; 435/375; 514/44
(58) Field of Classification Search .............. None
See application file for complete search history.

(56) References Cited

U.S. PATENT DOCUMENTS

| | | | |
|---|---|---|---|
| 3,687,808 A | 8/1972 | Merigan, Jr. et al. | 195/28 |
| 3,791,932 A | 2/1974 | Schuurs et al. | 195/103.5 |
| 3,839,153 A | 10/1974 | Schuurs et al. | 195/103.5 |
| 3,850,578 A | 11/1974 | McConnell | 23/230 |
| 3,850,752 A | 11/1974 | Schuurs et al. | 195/103.5 |
| 3,853,987 A | 12/1974 | Dreyer | 424/1 |
| 3,867,517 A | 2/1975 | Ling | 424/1 |
| 3,879,262 A | 4/1975 | Schuurs et al. | 195/63 |
| 3,901,654 A | 8/1975 | Gross | 23/230 |
| 3,935,074 A | 1/1976 | Rubenstein et al. | 195/103.5 |
| 3,984,533 A | 10/1976 | Uzgiris | 424/12 |
| 3,996,345 A | 12/1976 | Ullman et al. | 424/12 |
| 4,034,074 A | 7/1977 | Miles | 424/1 |
| 4,098,876 A | 7/1978 | Piasio et al. | 424/1 |
| 4,469,863 A | 9/1984 | Ts'o et al. | 536/27 |
| 4,476,301 A | 10/1984 | Imbach et al. | 536/27 |
| 4,666,828 A | 5/1987 | Gusella | 435/6 |
| 4,683,202 A | 7/1987 | Mullis | 435/91 |
| 4,801,531 A | 1/1989 | Frossard | 435/6 |
| 4,873,316 A | 10/1989 | Meade et al. | 530/412 |
| 4,879,219 A | 11/1989 | Wands et al. | 435/7 |
| 5,011,771 A | 4/1991 | Bellet et al. | 435/7.94 |
| 5,023,243 A | 6/1991 | Tullis | 514/44 |
| 5,034,506 A | 7/1991 | Summerton et al. | 528/391 |
| 5,166,315 A | 11/1992 | Summerton et al. | 528/406 |
| 5,177,196 A | 1/1993 | Meyer, Jr. et al. | 536/22.1 |
| 5,185,444 A | 2/1993 | Summerton et al. | 544/81 |
| 5,188,897 A | 2/1993 | Suhadolnik et al. | 428/402.2 |
| 5,192,659 A | 3/1993 | Simons | 435/6 |
| 5,214,134 A | 5/1993 | Weis et al. | 536/25.3 |
| 5,216,141 A | 6/1993 | Benner | 536/27.13 |
| 5,235,033 A | 8/1993 | Summerton et al. | 528/391 |
| 5,264,423 A | 11/1993 | Cohen et al. | 514/44 |
| 5,264,562 A | 11/1993 | Matteucci | 536/23.1 |
| 5,264,564 A | 11/1993 | Matteucci | 536/23.1 |
| 5,272,057 A | 12/1993 | Smulson et al. | 435/6 |
| 5,276,019 A | 1/1994 | Cohen et al. | 514/44 |
| 5,278,302 A | 1/1994 | Caruthers et al. | 536/24.5 |
| 5,281,521 A | 1/1994 | Trojanowski | 395/142 |
| 5,286,717 A | 2/1994 | Cohen et al. | 514/44 |
| 5,321,131 A | 6/1994 | Agrawal et al. | 536/25.34 |
| 5,399,676 A | 3/1995 | Froehler | 536/23.1 |
| 5,405,938 A | 4/1995 | Summerton et al. | 528/406 |
| 5,405,939 A | 4/1995 | Suhadolnik et al. | 530/44 |
| 5,434,257 A | 7/1995 | Matteucci et al. | 536/24.3 |
| 5,453,496 A | 9/1995 | Caruthers et al. | 536/24.5 |
| 5,455,233 A | 10/1995 | Spielvogel et al. | 514/44 |
| 5,464,764 A | 11/1995 | Capecchi et al. | 435/172.3 |
| 5,466,677 A | 11/1995 | Baxter et al. | 514/44 |
| 5,470,967 A | 11/1995 | Huie et al. | 536/24.3 |
| 5,476,925 A | 12/1995 | Letsinger et al. | 536/23.1 |
| 5,487,992 A | 1/1996 | Capecchi et al. | 435/172.3 |
| 5,489,677 A | 2/1996 | Sanghvi et al. | 536/22.1 |

(Continued)

FOREIGN PATENT DOCUMENTS

EP        375408        6/1990

(Continued)

OTHER PUBLICATIONS

International Search Report Appln. No. PCT/IL06/00785. International Search Report Appln. No. PCT/IL06/00785.
N. Berteaux et al, "H19 mRNA-like non-coding RNA promotes breast cancer cell proliferation through positive control by E2F1", The Journal of Biological Chemistry , vol. 280, No. 33 Papers in Press, pp. 29625-29636 (2005).
U.S. Appl. No. 12/523,288, filed Jul. 15, 2009.
U.S. Appl. No. 12/523,298, filed Jul. 15, 2009.
U.S. Appl. No. 12/015,325, filed Jan. 16, 2008.
Ariel et al., 1994, Gynecol Oncol 53, 212-219.
Ariel et al., 2004, Mol Carcinog 41, 69-76.
Ayesh and Matouk et al., 2002, Mol Carcinog 35, 63-74.
Ayesh and Matouk et al., 2003, Mol Ther 7, 535-541.
Banerji et al., 1983, Cell 33, 729-740.
Beal, P. A. and Dervan, P.B., et al., 1991, Science 251, 1360-1363.
Bernstein et al., 2001, Nature 409, 363-366.
Besch et al., 2002, J Biol Chem 277, 32473-79.
Blythe, N. L. et al., 1996, J Anat 188( Pt 1), 65-74.
Brannan et al., 1990, Mol Cell Biol 10, 28-36.
Brantl, 2002, Biochem Biophys Act 1575, 15-25.

(Continued)

*Primary Examiner* — Kimberly Chong
(74) *Attorney, Agent, or Firm* — Winston & Strawn LLP

(57) ABSTRACT

The present invention provides isolated oligonucleotides capable of down-regulating a level of H19 mRNA in cancer cells. Articles of manufacture comprising agents capable of downregulating H19 mRNA in combination with an additional anti-cancer treatment are disclosed as well as methods of treating cancer by administering same.

6 Claims, 10 Drawing Sheets

U.S. PATENT DOCUMENTS

| | | | |
|---|---|---|---|
| 5,519,126 A | 5/1996 | Hecht | 536/24.3 |
| 5,536,821 A | 7/1996 | Agrawal et al. | 536/22.1 |
| 5,539,082 A | 7/1996 | Nielsen et al. | 530/300 |
| 5,541,306 A | 7/1996 | Agrawal et al. | 536/22.1 |
| 5,541,307 A | 7/1996 | Cook et al. | 536/23.1 |
| 5,550,111 A | 8/1996 | Suhadolnik et al. | 514/44 |
| 5,561,225 A | 10/1996 | Maddry et al. | 536/23.1 |
| 5,563,253 A | 10/1996 | Agrawal et al. | 536/22.1 |
| 5,571,799 A | 11/1996 | Tkachuk et al. | 514/47 |
| 5,587,361 A | 12/1996 | Cook et al. | 514/44 |
| 5,596,086 A | 1/1997 | Matteucci et al. | 536/22.1 |
| 5,602,240 A | 2/1997 | De Mesmaeker et al. | 536/22.1 |
| 5,608,046 A | 3/1997 | Cook et al. | 536/23.1 |
| 5,610,289 A | 3/1997 | Cook et al. | 536/25.34 |
| 5,618,704 A | 4/1997 | Sanghvi et al. | 435/91.5 |
| 5,623,070 A | 4/1997 | Cook et al. | 536/27.6 |
| 5,625,050 A | 4/1997 | Beaton et al. | 536/24.1 |
| 5,633,360 A | 5/1997 | Bischofberger et al. | 536/22.1 |
| 5,663,312 A | 9/1997 | Chaturvedula | 536/22.1 |
| 5,677,437 A | 10/1997 | Teng et al. | 536/23.1 |
| 5,677,439 A | 10/1997 | Weis et al. | 536/23.1 |
| 5,714,331 A | 2/1998 | Buchardt et al. | 435/6 |
| 5,719,262 A | 2/1998 | Buchardt et al. | 530/300 |
| 5,721,138 A | 2/1998 | Lawn | 435/325 |
| 5,955,273 A | 9/1999 | Hochberg et al. | 435/6 |
| 6,303,374 B1 | 10/2001 | Zhang et al. | 435/6 |
| 6,306,833 B1 | 10/2001 | Hochberg et al. | 514/44 |
| 6,326,174 B1 | 12/2001 | Joyce et al. | 435/91.31 |
| 6,506,559 B1 | 1/2003 | Fire et al. | 435/6 |
| 2002/0123476 A1 | 9/2002 | Emanuele et al. | 514/44 |
| 2002/0128218 A1 | 9/2002 | Emanuele et al. | 514/44 |
| 2003/0017068 A1 | 1/2003 | Larrain et al. | 417/567 |
| 2003/0096980 A1 | 5/2003 | Froehler et al. | 536/23.1 |
| 2003/0143732 A1* | 7/2003 | Fosnaugh et al. | 435/325 |
| 2003/0170680 A1 | 9/2003 | Froehler et al. | 435/91.1 |
| 2004/0082529 A1* | 4/2004 | Hochberg et al. | 514/44 |
| 2004/0259247 A1* | 12/2004 | Tuschl et al. | 435/375 |
| 2005/0042753 A1 | 2/2005 | Yang et al. | 435/455 |
| 2005/0118625 A1* | 6/2005 | Mounts | 435/6 |
| 2006/0083682 A1 | 4/2006 | Bergstein | 424/1.11 |
| 2006/0217331 A1 | 9/2006 | Vargeese et al. | 536/24.5 |
| 2006/0269518 A1 | 11/2006 | Chang et al. | 536/24.5 |

FOREIGN PATENT DOCUMENTS

| | | |
|---|---|---|
| EP | 264166 | 4/1998 |
| WO | WO 9524503 | 9/1995 |
| WO | WO 98/34613 | 8/1998 |
| WO | 99/18195 | 4/1999 |
| WO | WO 00/71707 A1 | 11/2000 |
| WO | 01/75164 | 10/2001 |
| WO | 02/44321 | 6/2002 |
| WO | 03/070897 | 8/2003 |
| WO | 2004/024957 | 3/2004 |
| WO | 2004/031359 | 4/2004 |
| WO | WO 2004003159 | 4/2004 |
| WO | 2005/079862 | 9/2005 |
| WO | 2005/112971 | 12/2005 |
| WO | WO 2005/113571 A1 | 12/2005 |
| WO | 2006/033561 | 3/2006 |
| WO | 2006/060454 | 6/2006 |
| WO | 2006/084027 | 8/2006 |
| WO | 2006/085700 | 8/2006 |
| WO | 2006/086345 | 8/2006 |
| WO | 2006/119266 | 11/2006 |
| WO | 2007/007317 | 1/2007 |
| WO | 2007/034487 | 3/2007 |

OTHER PUBLICATIONS

Breaker, R.R. and Joyce G., 1995, Chemistry and Biology 2, 655-660.
Byrne et al., 1989, Proc Natl Acad Sci USA 86, 5473-5477.
Calame et al., 1988, Adv. Immunol. 43, 235-275.
Carbone, et al., 2003, Nucl Acid Res 31, 833-43.
Cooney, M. et al., 1988 Science 241, 456-459.
Cullen, 2002, Nat Immunol 3, 597-599.
Edlund et al., 1985, Science 230, 912-916.
Gilboa et al., 1986, Biotechniques 4(6), 504-512.
Graveel et al., 2001, Oncogene 20, 2704-2712.
Hammond et al., 2001, Nat Rev Gen 2, 110-119.
Hutvagner and Zamore, 2002, Curr Opin Genetics and Development 12, 225-232.
Kaplan, R., et al., 2003, Cancer Res 63, 1475-1482.
Khachigian, L.M., 2002, Curr Opin Mol Ther 4, 119-21.
Liang, C.Y., et al., 2004, Arch Virol 149, 51-60.
Lottin et al, 2002, Carcinogesis 23, 1885-1895.
Lottin et al, 2002, Oncogene 21, 1625-1631.
Maher III, L. J., et al., 1989, Science 245, 725-730.
Matouk et al., 2005, Cancer Therapy 3, 249-266.
Matouk et al., 2006, Hepatology 44(4 Supp. 1), 529A.
Matouk et al., 2007, PLoS ONE 2(9), e845.
Moser, H.E., et al., 1987, Science 238, 645-650.
Pinkert et al., 1987, Genes Dev 1, 268-277.
Puri et al., 2001, J Biol Chem 276, 28991-98.
Rachmilewitz et al, 1995, Oncogene 11, 863-870.
Rodesch et al, 1992, Obstet Gynecol 80, 283-285.
Santoro, S.W. & Joyce, G.F., 1997, Proc Natl Acad Sci USA 94, 4262-4266.
Seidman and Glazer, 2003, J Clin Invest 112, 487-94.
Sharp, 2001, Genes Dev 15, 485-90.
Soreq et al., 1974, J Mol Bio 88, 233-45.
Stuhlmuller et al, 2003, Am J Pathol 163, 901-911.
Tonkinson et al., 1996, Cancer Investigation 14(1), 54-65.
Tuschl, 2001, ChemBiochem 2, 239-245.
Vasquez et al., 1999, Nucl Acids Res 27, 1176-81.
Vuyisich and Beal, 2000, Nuc Acids Res 28, 2369-74.
Welch et al., 1998, Clin Diagn Virol 10, 163-71.
Welch et al., 1998, Curr Opin Biotechnol 9, 486-96.
Winoto et al., 1989, EMBO J 8, 729-733.
Zabala, M. et al., 2004, Cancer Res 64(8), 2799-804.
Bennet M.J. et al., "Refined structure of dimeric diphtheria toxin at 2.0 A resolution", Protein Science 1994, 3(9):1444-1463.
Poirier F. et al., "The murine H19 gene is activated during embryonic stem cell differentiation in vitro and at the time of implantation in the developing embryo", Development 1991, 113(4):1105-14.
Scott R.E. et al., "De-differentiation-derived mesenchymal stem cells demonstrate selective repression in H19 bioregulatory RNA gene expression", Differentiation 2005, 73(6):294-302.
Heike Y. et al., XP008083577, "Overcoming Multi-Drug Resistance Using an Intracellular AntiMDR1 SFV", International Journal of Cancer, vol. 92 1, pp. 115-122, (2001).
Stein S. et al., XP004260296, "A Disulfide Conjugate Between Anti-Tetanus Antibodies and HIV (37-72) Tat Neutralizes Tetanus Toxin Inside Chromaffin Cells", FEBS Letters, vol., 458, pp. 383-386, (1999).
Astriab-Fisher A. et al., XP002259727, "Conjugates of Antisense Oligonucleotides with the Tat and Antennapedia Cell-Penetrating Peptides: Effects of Cellular Uptake, Binding to Target Sequences, and Biologic Actions", Pharmaceutical Research, vol. 19, No. 6, pp. 744-754, (2006).
Mie M. et al., XP004461154, "Intracellular Delivery of Antibodies Using Tat Fusion Protein A", Biochemical and Biophysical Research Communications, vol. 310, pp. 730-734 (2003).
Hu Meiduo et al., XP002477558, "HIV-1 Tat Peptide Immunoconjugates Differentially Sensitive Breast Cancer Cells to Selected AntiProliferative Agents that Induce the Cyclin-Dependent Kinase Inhibitor p21 $^{WAF-1/CIP-1}$" Bioconjugate Chemistry, vol. 17, No. 5, pp. 1280-1287, (2006).

\* cited by examiner

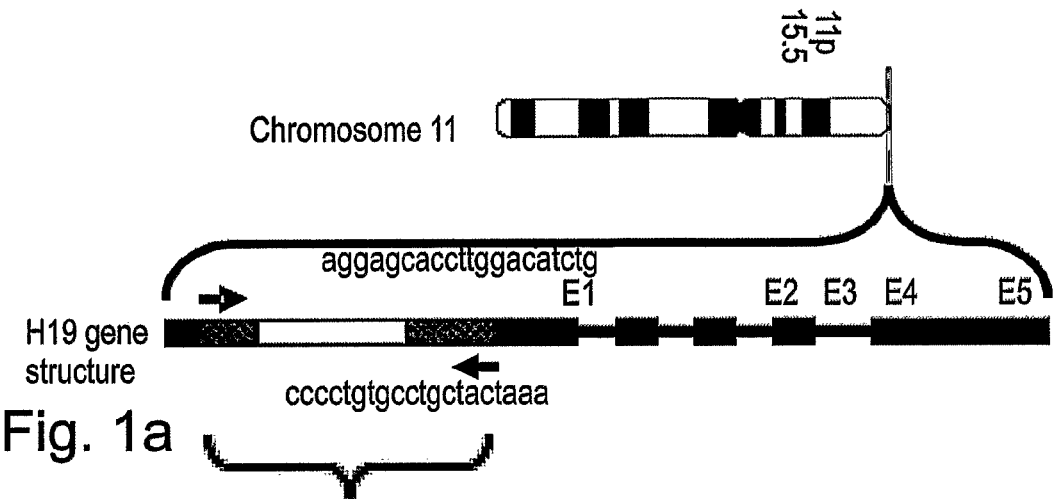
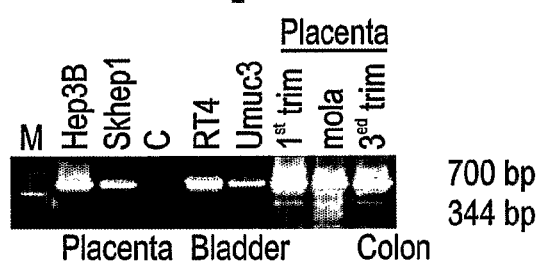
Fig. 1b
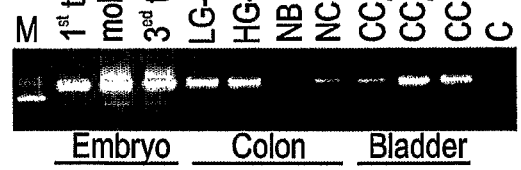
Fig. 1c
Fig. 1d
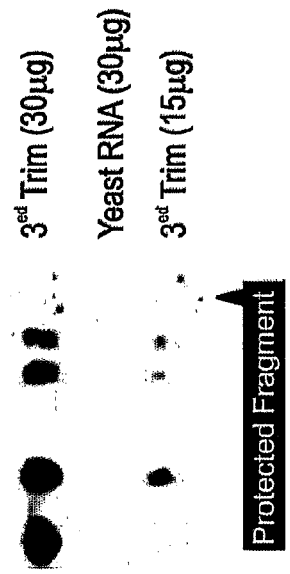
Fig. 1e
227_CAGGCATCGTGCAGACAGGGNGACATCTTCTCGGGGGGAGCCGAGA_608
Fig. 1f

FIGs. 2A-B
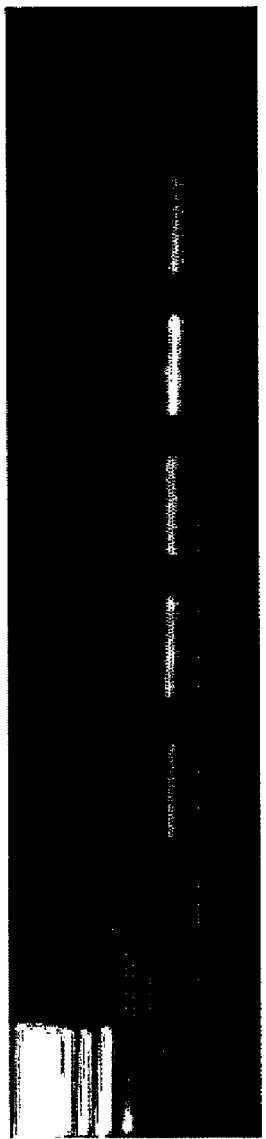
A
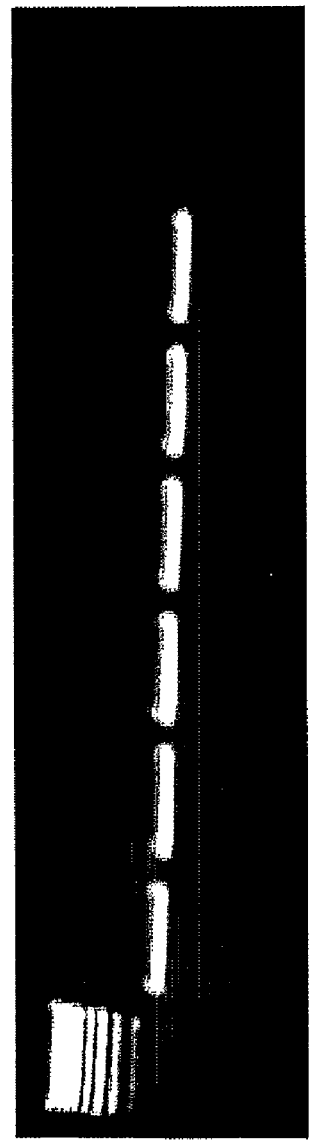
B

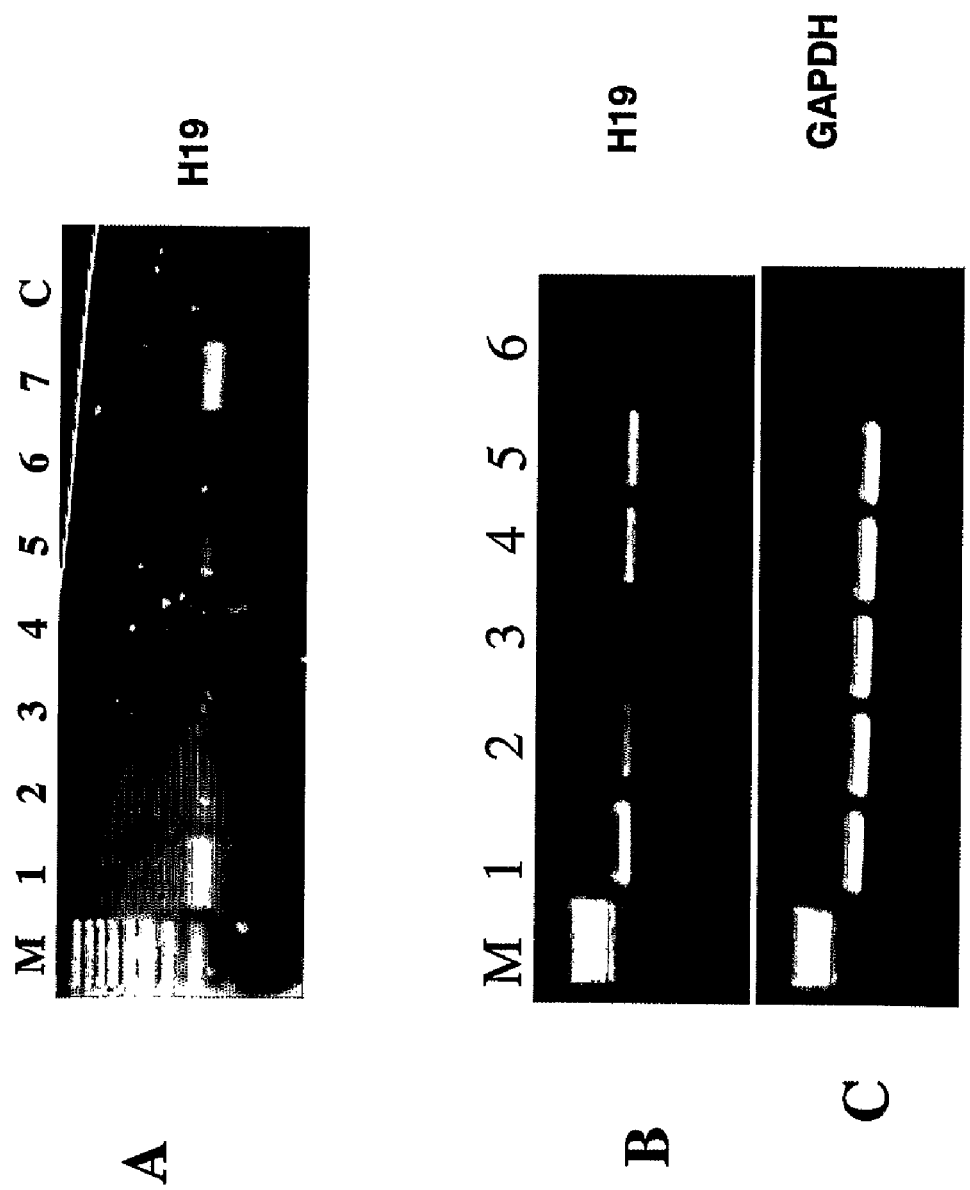
FIGS. 3A-C

FIGs. 3D-F
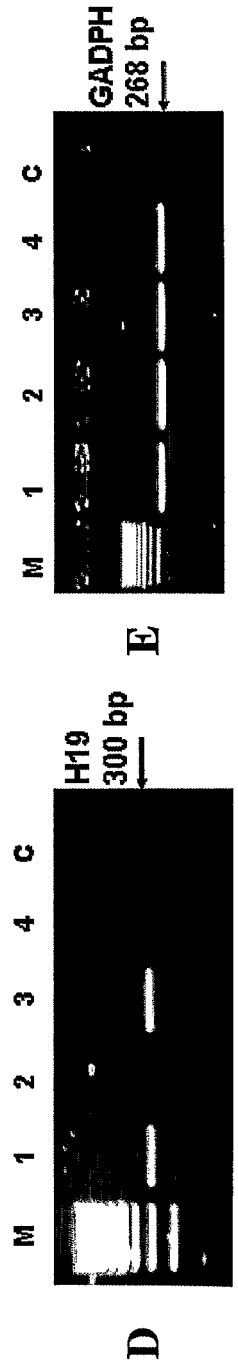
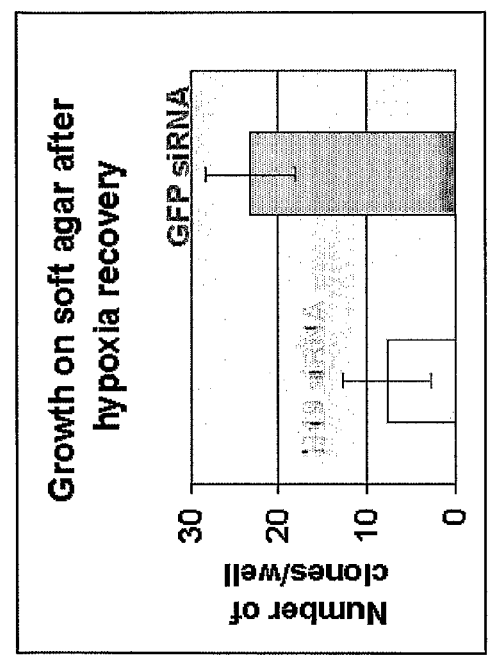

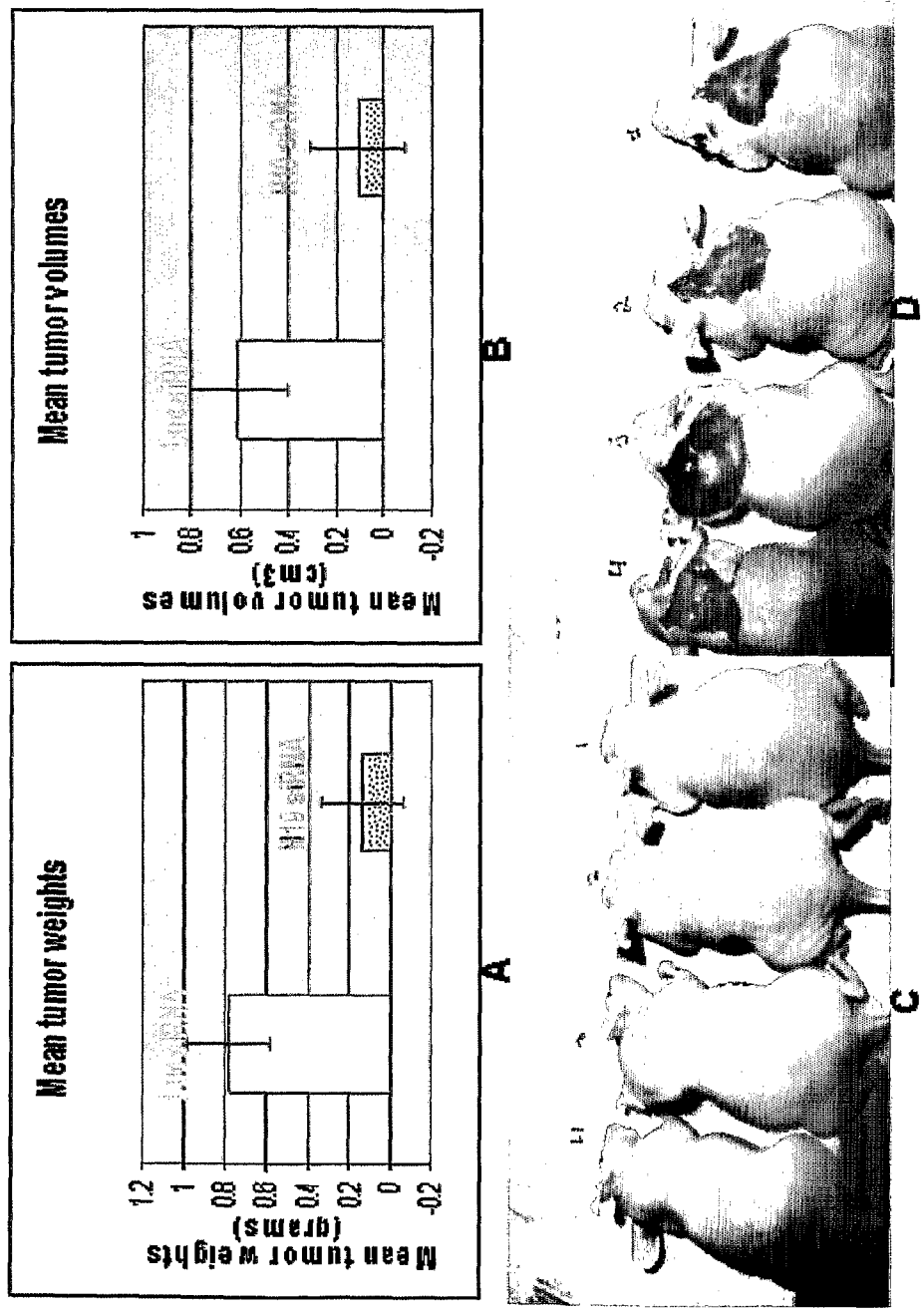
FIGs. 4A-D

FIGS. 5A-D
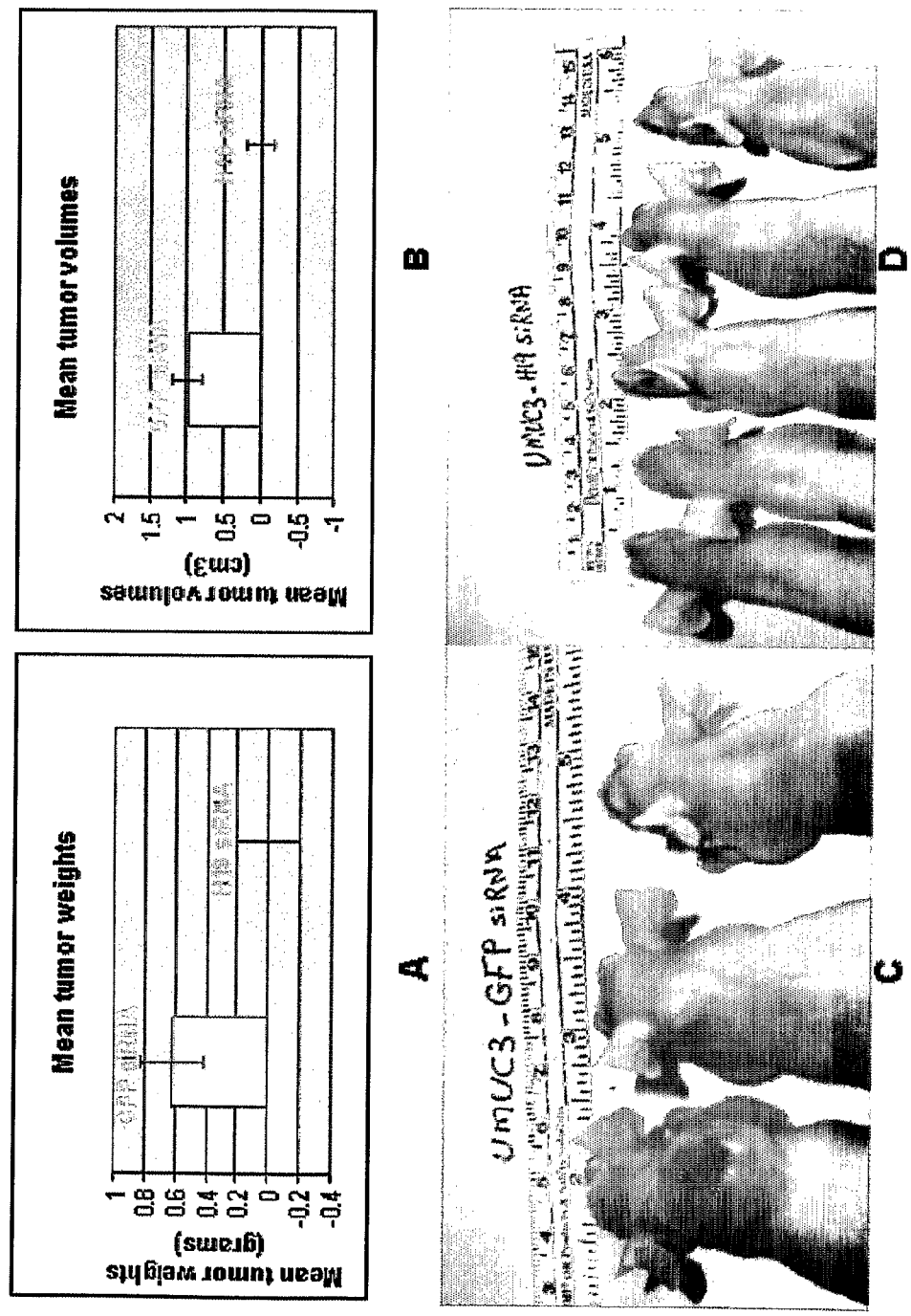

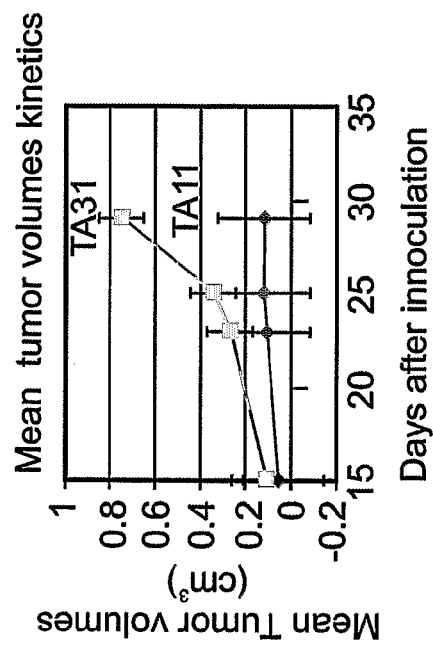
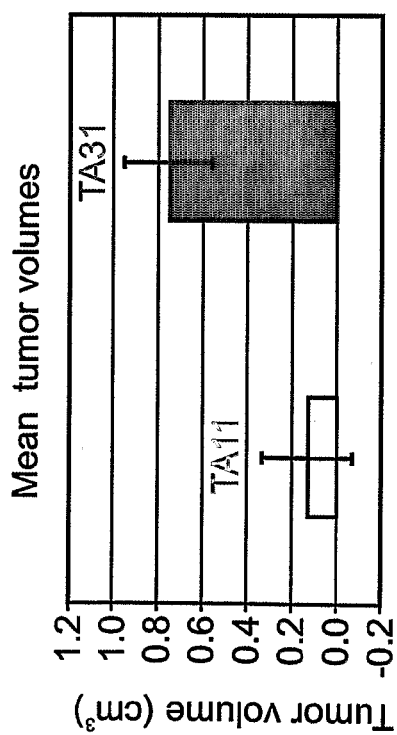
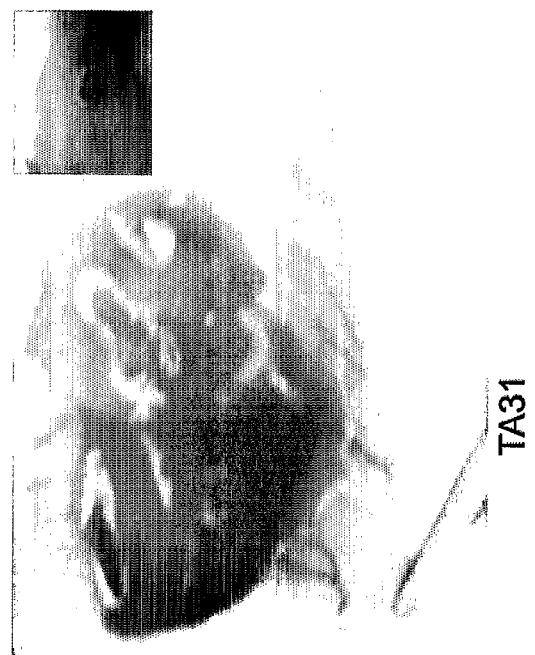
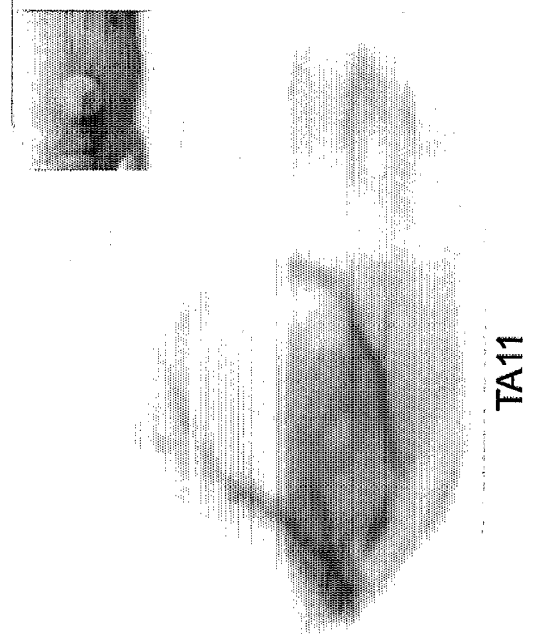
Fig. 8a
Fig. 8b
Fig. 8c
Fig. 8d

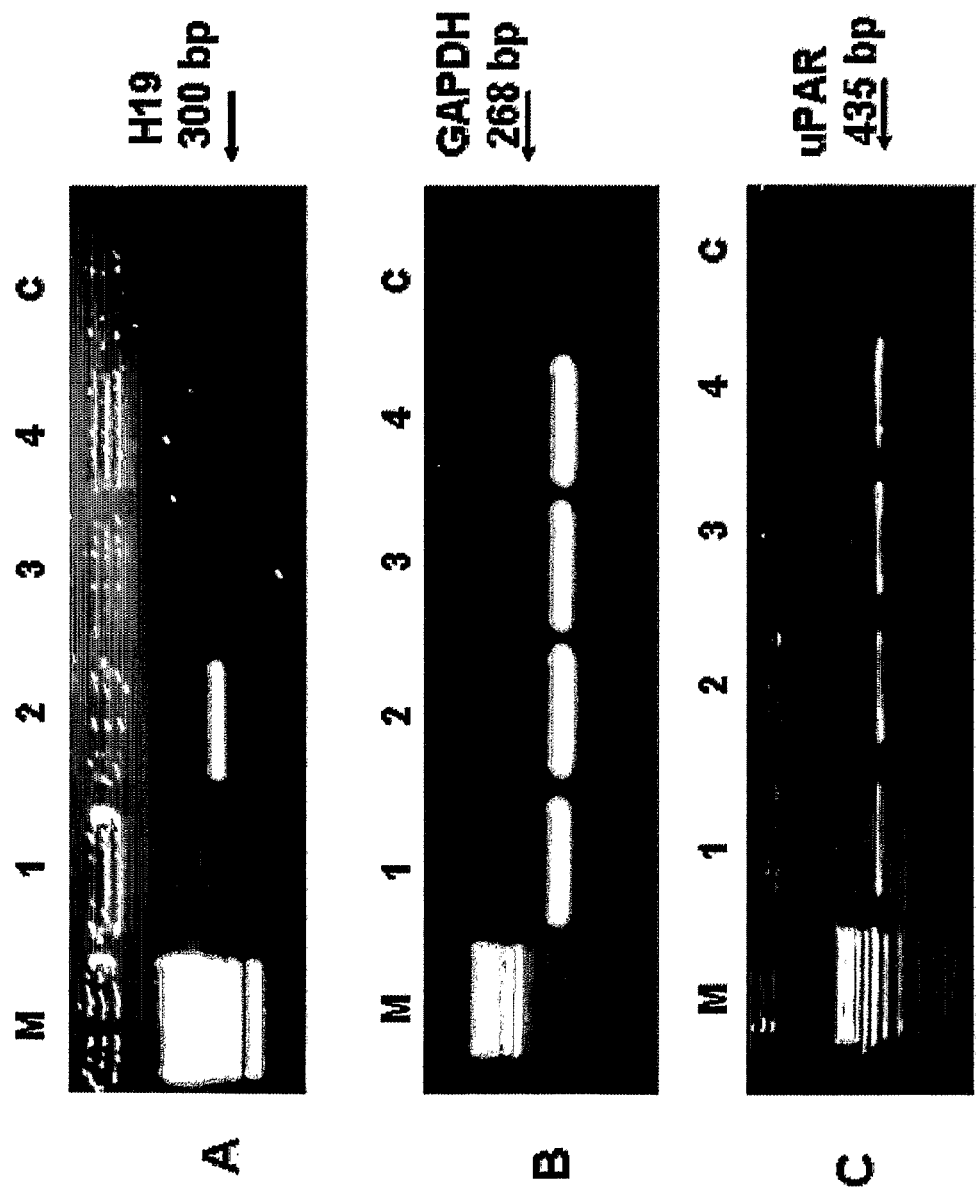
FIGs. 9A-C

SEQUENCE LISTING

<160> NUMBER OF SEQ ID NOS: 14

<210> SEQ ID NO 1
<211> LENGTH: 21
<212> TYPE: DNA
<213> ORGANISM: Artificial sequence
<220> FEATURE:
<223> OTHER INFORMATION: H19 targeting siRNA duplex

<400> SEQUENCE: 1
uaagucauuu gcacugguut t                                          21

<210> SEQ ID NO 2
<211> LENGTH: 21
<212> TYPE: DNA
<213> ORGANISM: Artificial sequence
<220> FEATURE:
<223> OTHER INFORMATION: H19 targeting siRNA duplex

<400> SEQUENCE: 2
gcaggacaug acauggucct t                                          21

<210> SEQ ID NO 3
<211> LENGTH: 21
<212> TYPE: DNA
<213> ORGANISM: Artificial sequence
<220> FEATURE:
<223> OTHER INFORMATION: H19 targeting siRNA duplex

<400> SEQUENCE: 3
ccaacaucaa agacaccaut t                                          21

<210> SEQ ID NO 4
<211> LENGTH: 21
<212> TYPE: DNA
<213> ORGANISM: Artificial sequence
<220> FEATURE:
<223> OTHER INFORMATION: H19 targeting siRNA duplex

<400> SEQUENCE: 4
ccaggcagaa agagcaagat t                                          21

```
<210> SEQ ID NO 5
<211> LENGTH: 21
<212> TYPE: DNA
<213> ORGANISM: Artificial sequence
<220> FEATURE:
<223> OTHER INFORMATION: Luciferase targeting siRNA duplex

<400> SEQUENCE: 5
cuuacgcuga guacuucgat t                                              21

<210> SEQ ID NO 6
<211> LENGTH: 22
<212> TYPE: DNA
<213> ORGANISM: Artificial sequence
<220> FEATURE:
<223> OTHER INFORMATION: GFP targeting siRNA duplex

<400> SEQUENCE: 6
gcaagcugac ccugaaguuc au                                             22

<210> SEQ ID NO 7
<211> LENGTH: 3489
<212> TYPE: DNA
<213> ORGANISM: Homo sapiens
<220> FEATURE:
<221> NAME/KEY: misc_feature
<222> LOCATION: (2599)..(2599)
<223> OTHER INFORMATION: n is a, c, g, or t
<220> FEATURE:
<221> NAME/KEY: misc_feature
<222> LOCATION: (2815)..(2815)
<223> OTHER INFORMATION: n is a, c, g, or t

<400> SEQUENCE: 7
ctgcagggcc ccaacaaccc tcaccaaagg ccaaggtggt gaccgacgga cccacagcgg      60
ggtggctggg ggagtcgaaa ctcgccagtc tccactccac tcccaaccgt ggtgcccac     120 gcgggcctgg gagagtctgt gaggccgccc accgcttgtc agtagagtgc gcccgcgagc    180
cgtaagcaca gcccggcaac atgcggtctt cagacaggaa agtggccgcg aatgggaccg    240
gggtgcccag cggctgtggg gactctgtcc tgcggaaacc gcggtgacga gcacaagctc    300
ggtcaactgg atgggaatcg gcctggggg ctggcaccgc gcccaccagg gggtttgcgg     360
cacttccctc tgcccctcag caccccaccc tactctcca ggaacgtgag gtctgagccg     420
tgatggtggc aggaagggc cctctgtgcc atccgagtcc ccagggaccc gcagctggcc     480
cccagccatg tgcaaagtat gtgcaggcg ctggcaggca gggagcagca ggcatggtgt      540
cccctgaggg gagacagtgg tctgggaggg agaggtcctg gaccctgagg gaggtgatgg      600
ggcaatgctc agccctgtct ccggatgcca aggagggt gcgggaggc cgtctttgga       660 gaattccagg atgggtgctg ggtgagagag acgtgtgctg gaactgtcca gggcggaggt     720
gggccctgcg ggggccctcg ggagggccct gctctgattg gccggcaggg caggggcggg     780
aattctggcg ggccacccca gttagaaaaa gcccgggcta ggaccgagga gcaggtgag     840 ggagggggtg ggatgggtgg ggggtaacgg gggaactgg ggaagtgggg aaccgagggg      900
caaccagggg aagatggggt gctggaggag agcttgtggg agccaaggag cacccttggac    960 atctggagtc tggcaggagt gatgacgggt ggaggggcta gctcgaggca gggctggtgg    1020
ggcctgaggc cagtgaggag tgtggagtag gtgcccaggc atcgtgcaga cagggcgaca    1080
tcagctgggg acgatgggcc tgagctaggg ctggaaagaa ggggagcca ggcattcatc     1140 ccggtcactt tggttacag gacgtggcag ctggttggac gaggggagct ggtgggcagg     1200
gtttgatccc agggcctggg caacggaggt gtagctggca gcagcgggca ggtgaggacc    1260
```

```
ccatctgccg ggcaggtgag tcccttccct ccccaggcct cgcttcccca gccttctgaa    1320
agaaggaggt ttaggggatc gagggctggc ggggagaagc agacaccctc ccagcagagg    1380
ggcaggatgg gggcaggaga gttagcaaag gtgacatctt ctcgggggga gccgagactg    1440
cgcaaggctg gggggttatg ggcccgttcc aggcagaaag agcaagaggg cagggaggga    1500
gcacaggggt ggccagcgta gggtccagca cgtggggtgg tacccaggcc ctgggtcaga    1560
cagggacatg gcagggggaca caggacagag gggtccccag ctgccacctc acccaccgca    1620
attcatttag tagcaggcac aggggcagct ccggcacggc tttctcaggc ctatgccgga    1680
gcctcgaggg ctggagagcg ggaagacagg cagtgctcgg ggagttgcag caggacgtca    1740
ccaggagggc gaagcggcca cgggaggggg gccccgggac attgcgcagc aaggaggctg    1800
cagggggctcg gcctgcgggc gccggtccca cgaggcactg cggcccaggg tctggtgcgg    1860
agagggccca cagtggactt ggtgacgctg tatgccctca ccgctcagcc cctggggctg    1920
gcttggcaga cagtacagca tccaggggag tcaagggcat ggggcgagac cagactaggc    1980
gaggcgggcg ggcggagtg aatgagctct caggagggag gatggtgcag gcaggggtga    2040
ggagcgcagc gggcggcgag cgggaggcac tggcctccag agcccgtggc caaggcgggc    2100
ctcgcgggcg gcgacggagc cgggatcggt gcctcagcgt tcgggctgga gacgagggtg    2160
agttttcccc cctctgccac cctcagcccc acccgccccc tccccacaca accaacacgt    2220
tctccccaca cgactctctc gttctcccca cagccaggtc tccagctggg gtggacgtgc    2280
ccaccagctg ccgaaggcca agacgccagg tccggtggac gtgacaagca ggacatgaca    2340
tggtccggtg tgacggcgag gacagaggag gcgcgtccgg ccttcctggt gagcgtgtct    2400
gccctccctg cgtcaggacg gccctgccca gaccgccccg cgccaccatc tcactgcccc    2460
gacctctgtc ttctacagaa caccttaggc tggtggggct gcggcaagaa gcgggtctgt    2520
ttctttactt cctccacgga gtcggcacac tatggctgcc ctctgggctc ccagaaccca    2580
caacatgaaa ggtgagggnc ttcctgccac acttggggtg ggggcacgc gagaggagct    2640
gagtgggacc tcaactcctt ccccatccac agaaatggtg ctacccagct caagcctggg    2700
cctttgaatc cggacacaaa accctctagc ttggaaatga atatgctgca ctttacaacc    2760
actgcactac ctgactcagg aatcggctct ggaaggtgag caccagcgct ccttnggaag    2820
cctccaggcc cccgagcacc ctgcccccat cccacccacg tgtcgctatc tctaggtgaa    2880
gctagaggaa ccagacctca tcagcccaac atcaaagaca ccatcggaac agcagcgccc    2940
gcagcaccca ccccgcaccg gcgactccat cttcatggcc acccctgcg gtggacggtt    3000
gaccaccagc caccacatca tcccagagct gagctcctcc agcgggatga cgccgtcccc    3060
accacctccc tcttcttctt tttcatcctt ctgtctcttt gtttctgagc tttcctgtct    3120
ttccttttttt ctgagagatt caaagcctcc acgactctgt ttccccgtc ccttctgaat    3180
ttaatttgca ctaagtcatt tgcactggtt ggagttgtgg agacgccctt gagtctcagt    3240
acgagtgtgc gtgagtgtga gccaccttgg caagtgcctg tgcagggccc ggccgccctc    3300
catctgggcc gggtgactgg gcgccggctg tgtcccgag gcctcaccct gccctcgcct    3360
agtctggaag ctccgaccga catcacggag cagccttcaa gcattccatt acgccccatc    3420
tcgctctgtg cccctcccca ccagggcttc agcaggagcc ctggactcat catcaataaa    3480
cactgttac                                                            3489

<210> SEQ ID NO 8
<211> LENGTH: 20
```

```
<212> TYPE: DNA
<213> ORGANISM: Artificial sequence
<220> FEATURE:
<223> OTHER INFORMATION: Single strand DNA oligonucleotide

<400> SEQUENCE: 8
aggagcacct tggacatctg                                              20

<210> SEQ ID NO 9
<211> LENGTH: 20
<212> TYPE: DNA
<213> ORGANISM: Artificial sequence
<220> FEATURE:
<223> OTHER INFORMATION: Single strand DNA oligonucleotide

<400> SEQUENCE: 9
cccctgtgcc tgctactaaa                                              20

<210> SEQ ID NO 10
<211> LENGTH: 16
<212> TYPE: DNA
<213> ORGANISM: Artificial sequence
<220> FEATURE:
<223> OTHER INFORMATION: Single strand DNA oligonucleotide

<400> SEQUENCE: 10
ccggccttcc tgaaca                                                  16

<210> SEQ ID NO 11
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 11
ttccgatggt gtctttgatg t                                            21

<210> SEQ ID NO 12
<211> LENGTH: 21
<212> TYPE: DNA
<213> ORGANISM: Artificial sequence
<220> FEATURE:
<223> OTHER INFORMATION: Single strand DNA oligonucleotide

<400> SEQUENCE: 12
tctccagaac atcatccctg c                                            21

<210> SEQ ID NO 13
<211> LENGTH: 24
<212> TYPE: DNA
<213> ORGANISM: Artificial sequence
<220> FEATURE:
<223> OTHER INFORMATION: Single strand DNA oligonucleotide

<400> SEQUENCE: 13
gggtgtcgct gttgaagtca gagg                                         24

<210> SEQ ID NO 14
<211> LENGTH: 47
<212> TYPE: DNA
<213> ORGANISM: Artificial Sequence
<220> FEATURE:
<223> OTHER INFORMATION: fragment of splice variant
<220> FEATURE:
<221> NAME/KEY: misc_feature
<222> LOCATION: (21)..(21)
<223> OTHER INFORMATION: n is a, c, g, t or u
```

```
<400> SEQUENCE: 14
caggcatcgt gcagacaggg ncgacatctt ctcggggga gccgaga                              47
```

NUCLEIC ACID AGENTS FOR DOWNREGULATING H19 AND METHODS OF USING SAME

This application is a 371 filing of International Patent Application PCT/IL2006/000785, filed Jul. 6, 2006, which claims the benefit of U.S. application No. 60/696,795 filed Jul. 7, 2005.

FIELD AND BACKGROUND OF THE INVENTION

The present invention relates to nucleic acid agents for downregulating H19 and use thereof for the treatment of cancer.

H19 was the first human imprinted non protein-coding gene to be identified showing expression of only the maternal allele. It is also imprinted in mice. H19 was mapped on the short arm of the human chromosome 11, band 15.5, homologous to a region of murine chromosome 7. It belongs to a group of genes that very likely does not code for a protein product. H19 gene is abundantly expressed in embryogenesis but is shut off in most tissues after birth. However, studies of various tumors have demonstrated a re-expression or an over-expression of the H19 gene when compared to healthy tissues. Moreover in cancers of different etiologies and lineages, aberrant expression in allelic pattern was observed in some cases. While H19 shows mono-allelic expression in most tissues throughout development, with the exception of germ cells at certain stages of maturation, and in extra-villous trophoblasts, bi-allelic expression of this gene, referred as "relaxation of imprinting" or "loss of imprinting" (LOI), have been found in an increasing number of cancers, for example, hepatocellular carcinoma, liver neoplasms of albumin SV40 T antigen-transgenic rats, lung adenocarcinoma, esophageal, ovarian, rhabdomyosarcoma, cervical, bladder, head and neck squamous cell carcinoma, colorectal, uterus and in testicular germ cell tumors. Today nearly 30 types of cancers show dysregulated expression of H19 gene as compared to healthy tissues, with or without LOI. For a recent review see Matouk et al (Matouk et al, 2005, Gene Ther Mol Biol).

It was also shown that H19 over-expression of ectopic origin conferred a proliferative advantage for breast epithelial cells in a soft agar assay and in several combined immunodeficient (SCID) mice (Lottin et al, 2002, Oncogene 21, 1625-1631). In tumors formed by the injection of cells of a choriocarcinoma-derived cell line (JEG-3), and a bladder carcinoma cell line (T24P), the H19 level is very high when compared to the level of H19 in cells prior to injection [Rachmilewitz et al, 1995, Oncogene 11, 863-870].

Moreover, certain known carcinogens upregulate the expression of the H19 gene. A dramatic elevation of H19 RNA levels was detected in the airway epithelium of smokers without (LOI) [Kaplan et al, 2003, Cancer Res 63, 1475-1482]. BBN (a known carcinogen of the bladder) also induces the expression of H19 gene in the rat model of bladder cancer [Ariel et al, 2004, Mol Carcinog 41, 69-76]. Likewise, Diethylnitrosamine (a known carcinogen of the liver) induces the expression of H19 in a mice model of hepatocellular carcinoma [Graveel et al, 2001, Oncogene 20, 2704-2712]. All of these observations and others contradict the initial proposal that H19 is a tumor suppressor gene.

Comparing patterns of gene expression in two homogeneous cell populations that only differ in the presence or absence of H19 RNA have identified plenty of downstream effectors of H19 RNA, among these are group of genes that were previously reported to play crucial roles in some aspects of the tumorigenic process. H19 RNA presence may enhance the invasive, migratory and angiogenic capacity of the cell by up regulating genes that function in those pathways, and could thus contribute at least to the initial steps of the metastatic cascade. Additional studies highlight H19's potential role in promoting cancer progression and tumor metastasis by being a responsive gene to HGF/SF.

The specific expression of H19 gene in cancer cells has prompted its use in clinical applications for diagnosing cancer.

Thus, U.S. Pat. No. 5,955,273 to the present inventors teaches the use of H19 gene as a tumor specific marker.

PCT Pub. No. WO 9524503 teaches the detection of malignancies and their grading with a H19 gene probe by in-situ hybridization—useful for detecting presence/absence of malignancy in pediatric Wilms' Tumor.

PCT Pub. No. WO 0403159 teaches down-regulation of H19 for treating diseases associated with angiogenesis, such as cancer. However, down-regulation of H19 was not shown to reduce tumor size or volume, neither was specific and efficacious siRNA agents capable of down-regulating H19 taught. Furthermore, PCT Pub. No. WO 0403159 does not teach use of anti H19 agents as part of a combination therapy for treating cancer.

There is thus a widely recognized need for, and it would be highly advantageous to have, methods and compositions for down-regulating H19 for cancer treatment.

SUMMARY OF THE INVENTION

According to one aspect of the present invention there is provided an isolated oligonucleotide selected from the group consisting of SEQ ID NO: 1, 2, 3 and 4.

According to another aspect of the present invention there is provided a pharmaceutical composition comprising, a pharmaceutically acceptable carrier and as an active ingredient at least one isolated oligonucleotide selected from the group consisting of SEQ ID NO: 1, 2, 3 and 4.

According to yet another aspect of the present invention there is provided a use of an isolated oligonucleotide selected from the group consisting of SEQ ID NO: 1, 2, 3 and 4 for the preparation of a medicament for the treatment of cancer.

According to still another aspect of the present invention there is provided a method of treating cancer comprising:

(a) administering to, or expressing in cells of a subject in need thereof a therapeutically effective amount of an agent capable of down-regulating a level and/or activity of H19 mRNA, and (b) providing to the subject a cancer therapy, thereby treating cancer.

According to an additional aspect of the present invention there is provided a use of an agent capable of down-regulating a level and/or activity of H19 mRNA for the preparation of a medicament for the treatment of cancer in combination with a cancer therapy.

According to yet an additional aspect of the present invention there is provided a method of treating cancer comprising administering to, or expressing in cells of a subject in need thereof a therapeutically effective amount of at least one oligonucleotide selected from the group consisting of SEQ ID NO: 1, 2, 3 and 4, thereby treating cancer.

According to still an additional aspect of the present invention there is provided an article of manufacture comprising an agent capable of downregulating a level and/or activity of H19 mRNA and an additional anti cancer agent identified for treating cancer.

According to further features in preferred embodiments of the invention described below, the agent capable of down-regulating a level and/or activity of H19 mRNA is a nucleic acid agent.

According to still further features in the described preferred embodiments, the nucleic acid agent is selected from the group consisting of:

(a) a single stranded polynucleotide for inhibiting the transcription of the H19 RNA from the H19 gene;

(b) a single stranded polynucleotide for hybridizing to the H19 mRNA thereby leading to a reduction of H19 mRNA activity;

(c) a double stranded polynucleotide, leading to degradation of the H19 mRNA;

(d) a triplex forming polynucleotide for cleaving the H19 mRNA;

(e) a catalytic polynucleotide for cleaving the H19 mRNA;

(f) a single stranded polynucleotide for hybridizing to the H19 mRNA leading to enzymatic degradation thereof; and (g) nucleic acid sequences coding for any one of (a) to (f).

According to still further features in the described preferred embodiments, the nucleic acid agent is selected from the group consisting of an siRNA, a ribozyme and a DNAzyme.

According to still further features in the described preferred embodiments, the nucleic acid agent is a siRNA.

According to still further features in the described preferred embodiments, the siRNA comprises a nucleic acid sequence selected from the group consisting of SEQ ID NO: 1-4.

According to still further features in the described preferred embodiments, the administering is effected in situ.

According to still further features in the described preferred embodiments, the cancer is selected from the group consisting of pediatric solid tumors, Wilms' tumor, Hepatoblastoma, Embryonal rhabdomyosarcoma, Germ cell tumors and trophoblastic tumors, testicular germ cells tumors, immature teratoma of ovary, sacrococcygeal tumors, Choriocarcinoma, Placental site trophoblastic tumors, Epithelial adult tumors, Bladder carcinoma, Hepatocellular carcinoma, Ovarian carcinoma, Cervical carcinoma, Lung carcinoma, Breast carcinoma, Squamous cell carcinoma in head and neck, Esophageal carcinoma, Neurogenic tumor, Astrocytoma, Ganglioblastoma, Neuroblastoma.

According to still further features in the described preferred embodiments, the cancer is a bladder carcinoma or a hepatocellular carcinoma.

According to still further features in the described preferred embodiments, the agent capable of downregulating a level and/or activity of H19 mRNA is co-formulated with the additional anti cancer agent.

The present invention successfully addresses the shortcomings of the presently known configurations by providing nucleotide agents capable of down-regulating H19 RNA both alone and in combination for the treatment of cancer.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-F are photographs and schematic diagrams illustrating the presence of an alternative splice variant of H19 in human embryonic and placental specimens. FIG. 1A is a schematic representation of chromosome 11 showing the location of the H19 gene, which is composed of 5 exons (E1-5) (solid boxes) and 4 short introns (lines between boxes). The position of primers used in the PCR reaction (SEQ ID NOs: 8 and 9) are marked by horizontal arrows and are 117 and 816 bases downstream to the transcription initiation site. The spliced segment lacking is indicated by a grey box. FIGS. 1B-D are photographs of ethidium bromide stained gel for RT-PCR reaction. The following cells were analyzed: Hep3B and SKHep1 (hepatocellular carcinomas cell lines); RT4 and Umuc3 (bladder carcinoma cell lines); placental specimens: $1^{st}$ trim (first trimester); Mola, hydatiform mole; $3^{rd}$ trim (third trimester); LG-BC, low grade bladder cancer; HG-BC, high-grade bladder cancer; NB, normal bladder; NC, normal colon; CClym, colon cancer metastasized to lymph node; CCliv colon cancer metastasized to liver; CC, colon cancer; In FIGS. 1B-D, the lanes marked by C refer to a negative control; M refers to marker 100 bp ladder. The sizes of the products are indicated on the right. FIG. 1E is a photograph of an RNase protection assay. Arrowhead indicates the presence of the alternative splice variant 344 bases in third trimester placental tissue. Two other excessive additional bands, which could indicate the presence of another alternative splice variant, which were undetectable by RT-PCR reaction, were also detected. FIG. 1F is a partial sequence analysis (SEQ ID NO: 14) of the alternative spliced variant revealing a skipping region of 366 bases from exon 1. The underlined sequence indicates the splice junction. (Nucleotide numbering begins at the start codon).

FIGS. 2A-B are photographs of ethidium bromide stained gels illustrating the effect of increasing concentrations of $CoCl_2$ on the expression level of H19 RNA in Hep3B cells. FIG. 2A illustrates the RT-PCR products of the H19 gene in Hep3B cells. FIG. 2B illustrates the RT-PCR products of the GADPH gene as a positive control for RT-PCR integrity in Hep3B cells For FIGS. 2A and 2B, untreated Hep3B (lane1); 50, 100, 200, 300 and 400 µM $CoCl_2$ treated cells (lanes 2, 3, 4, 5 and 6) respectively.

FIGS. 3A-F are bar graphs and photographs illustrating the effectiveness of in-vitro down-regulation of H19 using the siRNAs of the present invention. FIGS. 3A-C are ethidium bromide stained gels illustrating the effect of different H19 siRNA duplexes on the expression level of H19 in a Hep3B cell line under normal culture condition (FIG. 3A) and hypoxia mimicking condition (FIG. 3B) as tested by RT-PCR analysis. FIG. 3A illustrates Hep3B cells transfected with unrelated siRNA duplex that targets luciferase gene (lane 1)

and with the four H19 siRNA duplexes (Lanes 2-5) (SEQ ID NOs. 1-4) and their equimolar mixtures (lane 6), and lipofectamine 2000 without siRNA (Mock) (Lane 7). Note, all siRNA agents tested (SEQ ID NOs: 1-4) were at least 50% effective in reducing the mRNA level of H19. C=PCR blank. FIGS. 3B and 3C illustrate Hep3B cells transfected in normal medium with siRNA duplex that targets luciferase gene—(SEQ ID NO: 5) (Lanes 1 and 5) and with 3 different H19 siRNA duplexes (SEQ ID NOs. 1, 3, and 4) (lanes 2-4). 24 hour post transfection, media was changed and 100 µM CoCl2 containing media was added except for lane 5 which shows cells which continued to grow in normal culture media. The incubation was for a further 22 hours. RT-PCR products are shown for both H19 (FIG. 3B) and GADPH (FIG. 3C) genes as a positive control for RT-PCR integrity.

FIGS. 3D-E are ethidium bromide stained gels illustrating the effect of H19 siRNA duplexes (SEQ ID NO:1) on the expression level of H19 in a UMUC3 cell line under normal culturing conditions and hypoxic conditions as tested by RT-PCR analysis. For FIGS. 3F and 3G, GFP siRNA transfected UMUC3 cells (lane 1), plus H19 siRNA—SEQ ID NO: 1 (lane 2) in normoxic conditions, and GFP siRNA transfected UMUC3 cells (lane 3), plus H19 siRNA (lane 4) in hypoxic conditions respectively.

FIG. 3F is a bar graph illustrating the reduction in colony numbers following hypoxia recovery following H19 siRNA (SEQ ID NO:3) transfection in Hep3B cells as compared to GFP siRNA control treated cells.

FIGS. 4A-D are bar graphs and photographs illustrating that transient H19 RNA downregulation in Hep3B cells inhibits tumorigenicity in vivo. Hep3B cells were transiently transfected with H19 siRNA 3 (SEQ ID NO: 3) or anti-Luc siRNA (SEQ ID NO: 5). Forty eight hours post transfection, cells were washed twice with PBS, trypsinized and counted. $1.5 \times 10^6$ cells receiving anti-H19 siRNA and anti-Luc siRNA were injected subcutaneously into the dorsal part of CD-1 nude mice (n=7 for both, and 4 for mock transfected). Palpable tumors were observed 15 days post inoculation in mice inoculated with Hep3B, transiently transfected with anti-Luc siRNA. Tumor volumes were followed up and measured using a caliper until day 30 post inoculation, after which mice were sacrificed. Significant (p<0.03) reductions of about 82% of both mean tumor weights (A) (±standard error) and mean tumor volumes (p<0.03) (B) (±standard error) were observed. Values represent end-points just prior to and following sacrificing animals. Shown are also representative features of tumors in 2 mice of each group (mice 1 and 2 are the H19 siRNA3 (SEQ ID NO: 3) treated animals, and mice 3 and 4 are the anti-Luc siRNA (SEQ ID NO: 5) treated animals) prior to tumor surgical exposure (C), and following exposure of their internal tumors (D).

FIGS. 5A-D are bar graphs and photographs illustrating the in vivo effect of siRNA-H19 on human bladder carcinoma cells-UMUC3. One million UMUC3 cells were injected subcutaneously to athymic mice (n=3 for GFP siRNA (SEQ ID NO; 6), and 5 for siRNA H19 (SEQ ID No:1), 48 hours after transiently transfected with siRNAs. Palable tumors were observed 6 weeks later in 2 out of 3 mice receiving UMUC3 transiently transfected with anti-GFP-siRNA, while in none of those receiving siRNA H19 (n=5). Mice were sacrificed 8 week after inoculation. Mean tumor volumes (B, P<0.05), and mean tumor weights (A, p<0.06) are depicted. Values represent end-points just before and after sacrificing animals. Pictures depict the external features of the tumors in mice inoculated with UMUC3 transfected with anti-GFP siRNA (C), and siRNA H19 (D).

FIG. 7A is a line graph depicting the change in tumor volume over time following injection of siRNA-H19 (SEQ ID NO: 1) or anti GFP siRNA into UMUC-3 treated mice. FIG. 7B is a bar graph depicting the change in tumor weight following injection of siRNA-H19 or anti GFP siRNA into UMUC-3 treated mice. FIG. 7C is a bar graph depicting tumor volume following injection of siRNA-H19 or anti GFP siRNA into Hep3B-treated mice. FIG. 7D is a bar graph depicting the change in tumor weight following injection of siRNA-H19 (SEQ ID NO: 3) or anti GFP siRNA into Hep3B treated mice.

FIGS. 8A-D are bar graphs and photographs illustrating the effect of H19 ectopic expression on the growth of the human bladder carcinoma cells TA11 (negative for H19) and TA31 (high expresser of H19) in vivo: Equal amounts ($2 \times 10^6$) of TA31H19-high and TA11H19-ve cells were implanted subcutaneously to CD-1 mice (n=5, each). Two weeks later, palable tumors appeared and tumor volumes were measured for additional two weeks using a caliper. Shown are end point measurements of the mean tumor volumes of the two groups (FIG. 8A), their mean tumor volumes kinetics (FIG. 8B), and a representative gross morphology of tumors derived from the TA11H19-ve (FIG. 8C) and TA31H19-high cells (FIG. 8D).

FIGS. 9A-C are photographs illustrating that H19 RNA is induced by hypoxic stress in Hep3B cell line and that siRNA directed against H19 very efficiently impedes its induction. Hep3B cells were seeded and transfected either with anti H19 siRNA or anti luc-siRNA. Twenty four hours post transfection, cells were either placed into an Aneoropack rectangular jar (Mitsubishi Chemical Company, Japan) to create a hypoxic-like condition within an hour, or left under normal oxygen concentration. Incubation lasted for 24 hours prior to RNA extraction. Shown are RT-PCR analyses for H19 RNA. FIG. 9A: Hep3B transfected with anti-luc siRNA (SEQ ID NO: 5) (lanes 1, 2) and anti H19 siRNA (SEQ ID NO: 3) (lanes 3, 4) both in normal (lanes 1, 3) and hypoxic (lanes 2, 4) culture conditions, respectively. PCR analysis of a housekeeping gene, GAPDH, (FIG. 9B), and uPAR (FIG. 9C).

DESCRIPTION OF THE PREFERRED EMBODIMENTS

The present invention relates to nucleic acid agents for downregulating the level and/or activity of H19 and pharmaceutical compositions and methods of using same. Specifically, the present invention relates to methods and compositions for treating cancer.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

H19 is an imprinted gene that demonstrates maternal monoallelic expression, and very likely does not code for a protein. It is abundantly expressed during embryogenesis and fetal development, but is typically shut off after birth in most tissues. However in an increasing numbers of cancers of different origins, expression of H19 RNA is up-regulated and an aberrant allelic pattern of expression was observed in some cases, suggesting that H19 may play a role in tumorigenesis.

While reducing the present method to practice, the present inventors designed through laborious bioinformatics modeling specific siRNAs which can effectively down-regulate H19 mRNA. The siRNAs of the present invention were selected using four different search engines to ensure that the optimal siRNAs were chosen.

As illustrated in FIG. 3A all the siRNAs that were generated were found to be efficient in down-regulating H19 mRNA. Furthermore, the present inventors showed that these siRNAs were able to down-regulate H19 mRNA under both normal and hypoxic conditions (FIGS. 3B-E). This is of particular relevance since tumor growth is associated with hypoxia, which in turn is associated with up-regulation of H19 RNA.

The siRNAs of the present invention were able to both prevent tumor formation and even reduce on-going disease by reduction of pre-established tumor volume and weight.

As illustrated in Example 4, administration of human carcinoma cells (Hep3B and UMUC3), previously transfected with H19 siRNA, into mice caused a very significant lowering in tumor weight (FIG. 4A and FIG. 5A) and volume (FIG. 4B and FIG. 5B) than administration of the identical cells transfected with control siRNA.

Figure 7B:
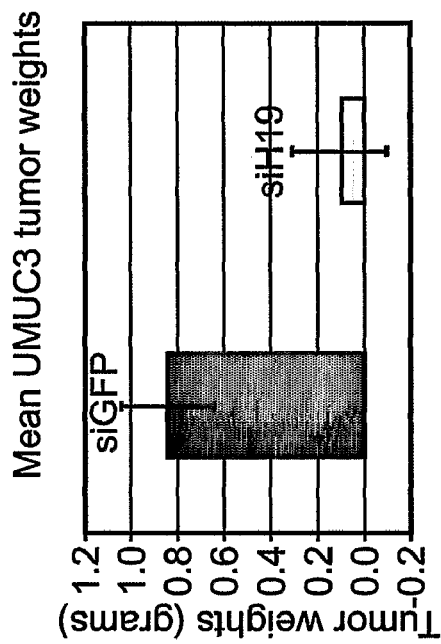
FIGS. 7A-D are bar and line graphs illustrating the effect of intratumoral administration of H19 siRNAs (SEQ ID No 1; SEQ ID NO: 3) or anti GFP siRNA (SEQ ID NO: 6) on previously injected human bladder carcinoma cells-UMUC3 (FIGS. 7A-B) SEQ ID NO: 1 and Hep3B cells SEQ ID NO: 3 (FIGS. 7C-D) in CD-1 nude mice.

Furthermore, as illustrated in Example 6, injection of H19 siRNA directly into tumors induced by UMUC3 cells, caused a very significant reduction of about 90% of mean tumor volumes (FIG. 7A), and of about 88% of mean tumor weights (FIG. 7B).

Figure 7D:
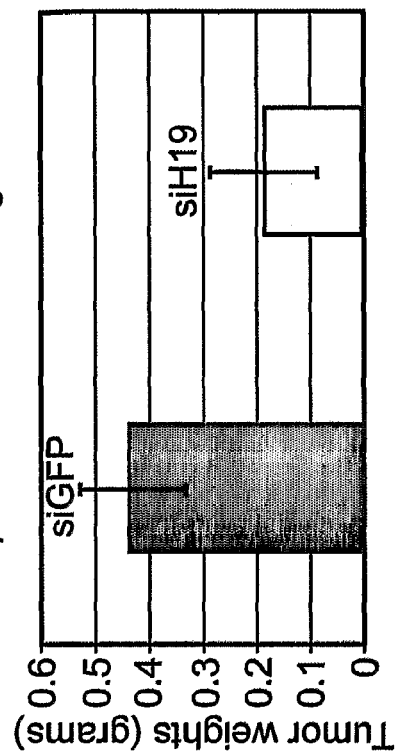

In Hep3B induced tumors, an approximate 40% reduction of tumor weights (FIG. 7C) and 56% reduction of tumor volumes (FIG. 7D) were observed following administration of H19 siRNA.

Altogether, these results undoubtedly place agents capable of down-regulating H19 as realistic candidates for both the prophylactic and therapeutic treatment of cancer.

Additionally, the present invention also envisages using agents capable of down-regulating H19 mRNA in combination therapy. It is well established that solid tumors especially those encountering hypoxic regions are resistant to cancer therapy. It is anticipated by the present invention anti H19 agents may act to sensitize a patient to a pre-established cancer therapy (e.g., radio-therapy, chemotherapy).

Thus according to one aspect of the present invention, there is provided an article of manufacture comprising an agent capable of downregulating a level and/or activity of H19 mRNA and an additional anti cancer agent identified for the treatment of cancer.

As used herein the term "treating" refers to preventing, alleviating or diminishing a symptom associated with a cancerous disease. Preferably, treating cures, e.g., substantially eliminates, the symptoms associated with cancer.

Any cancer which expresses H19 may be treated according to this aspect of the present invention. Preferable tumors treated according to the method of the present invention are those which express H19 mRNA during tumor onset or progression. Such tumors include, but are not limited to, Pediatric solid tumors, Wilms' tumor, Hepatoblastoma, Embryonal rhabdomyosarcoma, Germ cell tumors and trophoblastic tumors, testicular germ cells tumors, immature teratoma of ovary, sacrococcygeal tumors, Choriocarcinoma, Placental site trophoblastic tumors, Epithelial adult tumors, Bladder carcinoma, Hepatocellular carcinoma, Ovarian carcinoma, Cervical carcinoma, Lung carcinoma, Breast carcinoma, Squamous cell carcinoma in head and neck, Esophageal carcinoma, Neurogenic tumor, Astrocytoma, Ganglioblastoma, Neuroblastoma. Preferably the tumor is a bladder carcinoma or a hepatocellular carcinoma.

As used herein the term "subject" refers to any (e.g., mammalian) subject, preferably a human subject.

As used herein the phrase "H19 mRNA" refers to a transcriptional product of the H19 gene (GenBank Accession No. M32053—SEQ ID NO: 7).

The present inventors have identified a novel splice isoform of the H19RNA gene which is specifically expressed in embryonic tissues and not in carcinoma cells as demonstrated by RT-PCR analysis (FIGS. 1B-D) and RNase protection assay (FIG. 1E). This novel splice isoform was shown to lack part of exon-1 extending from nucleotide 252 to 588 of the transcription start site as compared to the known H19 transcript as set forth in SEQ ID NO: 7. Accordingly, the H19 RNA of this aspect of the present invention preferably comprises exon 1 of the H19 transcript and even more preferably comprises the RNA sequence denoted by nucleic acid sequence coordinates 252 to 588 of SEQ ID NO: 7.

Since H19 does not encode for a protein, downregulating a level or activity of H19mRNA is preferably effected at the RNA level.

Preferably the level and/or activity of H19 which is downregulated is greater than 10%, more preferably greater than 20%, more preferably greater than 40%, more preferably greater than 60%, more preferably greater than 80%, and even more preferably 100%.

Preferably the agent is a nucleic acid agent. More preferably the agent is an oligonucleotide, most preferably a double stranded oligonucleotide.

The decrease in the level of the H19 mRNA may be achieved by several mechanisms: by inhibiting transcription from the H19 gene to H19 RNA; by inhibition of the maturation process from hnRNA to mRNA; by promotion of mRNA degradation in the cytoplasm by enzymes (by forming RNA duplexes or triplexes, and by catalytic cleavage of nucleic acid based enzymes (DNAzymes and RNAzymes).

Thus the anti-H19 mRNA agent in accordance with the invention may be selected from the following:

1) a single stranded nucleic acid sequence for steric inhibition of the transcription of H19 RNA from its gene;
2) a single stranded nucleic acid sequence for hybridization with the H19 RNA leading to enzymatic degradation (for example by RNAses);
3) a double stranded nucleic acid sequence, that leads to degradation of the H19 (by forming siRNA);
4) a catalytic nucleic acid sequence for cleavage of the H19 mRNA;
5) a triplex forming nucleotide;
6) a single stranded nucleic acid sequence for hybridizing the H19 mRNA thereby leading to a reduction of H19 mRNA activity; and
7) nucleic acid sequences coding for any one of (1) to (6).

According to one embodiment of this aspect of the present invention the agent is a nucleic acid agent comprising a nucleic acid sequence capable of specifically hybridizing (e.g., in cells under physiological conditions) to the H19 RNA of the present invention, as described above.

As used herein, the term "nucleic acid agent" refers to a single-stranded or double-stranded oligomer or polymer of ribonucleic acid (RNA) or deoxyribonucleic acid (DNA) or mimetics thereof. This term includes polynucleotides composed of naturally occurring bases, sugars, and covalent internucleoside linkages (e.g., backbone), as well as polynucleotides having non-naturally occurring portions, which function similarly to respective naturally occurring portions.

As used herein, the phrase "capable of hybridizing" refers to base-pairing, where at least one strand of the nucleic acid agent is at least partly homologous to H19 mRNA.

Preferably, the nucleic acid agents of the present invention specifically hybridize with H19 RNA of the present invention i.e. have at least a 5 fold preference for hybridizing with H19 RNA as opposed to a non-related RNA molecule (e.g. GAPDH).

The nucleic acid agents designed according to the teachings of the present invention can be generated according to any nucleic acid synthesis method known in the art, including both enzymatic syntheses or solid-phase syntheses. Equipment and reagents for executing solid-phase synthesis are commercially available from, for example, Applied Biosystems. Any other means for such synthesis may also be employed; the actual synthesis of the nucleic acid agents is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

It will be appreciated that nucleic acid agents of the present invention can be also generated using an expression vector as is further described hereinbelow.

Preferably, the nucleic acid agents of the present invention are modified. Nucleic acid agents can be modified using various methods known in the art.

For example, the nucleic acid agents of the present invention may comprise heterocylic nucleosides consisting of purines and the pyrimidines bases, bonded in a 3'-to-5' phosphodiester linkage.

Preferably used nucleic acid agents are those modified either in backbone, internucleoside linkages, or bases, as is broadly described hereinunder.

Specific examples of preferred nucleic acid agents useful according to this aspect of the present invention include oligonucleotides or polynucleotides containing modified backbones or non-natural internucleoside linkages. Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'. Various salts, mixed salts, and free acid forms of the above modifications can also be used.

Alternatively, modified oligonucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other nucleic acid agents which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Nucleic acid agents of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

The nucleic acid agents of the present invention is of at least 10, at least 15, or at least 17 bases specifically hybridizable with H19 RNA. As illustrated in Example 1, the siRNAs of the present invention are 19 bases with two 3' overhangs.

It should be appreciated that the present invention also envisages agents other than nucleic acid agents that are capable of down-regulating H19 RNA such as knock-out agents.

A small interfering RNA (siRNA) molecule is an example of an nucleic acid agents agent capable of downregulating H19RNA. RNA interference is a two-step process. During the first step, which is termed the initiation step, input dsRNA is digested into 21-23 nucleotide (nt) small interfering RNAs (siRNA), probably by the action of Dicer, a member of the RNase III family of dsRNA-specific ribonucleases, which cleaves dsRNA (introduced directly or via an expressing vector, cassette or virus) in an ATP-dependent manner. Successive cleavage events degrade the RNA to 19-21 bp duplexes (siRNA), each strand with 2-nucleotide 3' overhangs [Hutvagner and Zamore Curr. Opin. Genetics and Development 12:225-232 (2002); and Bernstein Nature 409:363-366 (2001)].

In the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr. Opin. Genetics and Development 12:225-232 (2002); Hammond et al., (2001) Nat. Rev. Gen. 2:110-119 (2001); and Sharp Genes. Dev. 15:485-90 (2001)]. Although the mechanism of cleavage is still to be elucidated, research indicates that each RISC contains a single siRNA and an RNase [Hutvagner and Zamore Curr. Opin. Genetics and Development 12:225-232 (2002)].

It is possible to eliminate the "initiation step" by providing a priori siRNA.

Because of the remarkable potency of RNAi, an amplification step within the RNAi pathway has been suggested. Amplification could occur by copying of the input dsRNAs, which would generate more siRNAs, or by replication of the siRNAs formed. Alternatively or additionally, amplification could be effected by multiple turnover events of the RISC [Hammond et al., Nat. Rev. Gen. 2:110-119 (2001), Sharp Genes. Dev. 15:485-90 (2001); Hutvagner and Zamore Curr. Opin. Genetics and Development 12:225-232 (2002)]. For more information on RNAi see the following reviews Tuschl ChemBiochem. 2:239-245 (2001); Cullen Nat. Immunol. 3:597-599 (2002); and Brantl Biochem. Biophys. Act. 1575: 15-25 (2002).

Synthesis of RNAi molecules suitable for use with the present invention can be effected as follows. First, the H19 nucleic acid sequence target is scanned downstream for AA dinucleotide sequences. Occurrence of each AA and the 3' adjacent 19 nucleotides is recorded as potential siRNA target sites.

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites that exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

Examples of siRNAs which are capable of down-regulating H19 that may be used according to this aspect of the present invention are those set forth by SEQ ID NOs: 1-4.

Since these molecules were shown effective in reducing tumor size and volume the present invention also envisages treatment of cancer using these molecules alone and not necessarily in combination.

Another agent capable of downregulating the expression of a H19 RNA is a DNAzyme molecule capable of specifically cleaving its encoding polynucleotide. DNAzymes are single-stranded nucleic acid agents which are capable of cleaving both single and double stranded target sequences (Breaker, R. R. and Joyce, G. Chemistry and Biology 1995; 2:655; Santoro, S. W. & Joyce, G. F. Proc. Natl, Acad. Sci. USA 1997; 94:4262). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro, S. W. & Joyce, G. F. Proc. Natl, Acad. Sci. USA 199; for rev of DNAzymes see Khachigian, L M [Curr Opin Mol Ther 4:119-21 (2002)].

Examples of construction and amplification of synthetic, engineered DNAzymes recognizing single and double-stranded target cleavage sites have been disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh et al., 20002, Abstract 409, Ann Meeting Am Soc Gen Ther www.asgt.org). In another application, DNAzymes complementary to bcr-ab1 oncogenes were successful in inhibiting the oncogenes expression in leukemia cells, and lessening relapse rates in autologous bone marrow transplant in cases of Chronic Myelogenous Leukemia (CML) and Acute Lymphocytic Leukemia (ALL).

Another agent capable of downregulating H19RNA is a ribozyme molecule capable of specifically cleaving its encoding polynucleotide. Ribozymes are being increasingly used for the sequence-specific inhibition of gene expression by the cleavage of mRNAs encoding proteins of interest [Welch et al., Curr Opin Biotechnol. 9:486-96 (1998)]. The possibility of designing ribozymes to cleave any specific target RNA has rendered them valuable tools in both basic research and therapeutic applications. In the therapeutics area, ribozymes have been exploited to target viral RNAs in infectious diseases, dominant oncogenes in cancers and specific somatic mutations in genetic disorders [Welch et al., Clin Diagn Virol. 10:163-71 (1998)]. Most notably, several ribozyme gene therapy protocols for HIV patients are already in Phase 1 trials. More recently, ribozymes have been used for transgenic animal research, gene target validation and pathway elucidation. Several ribozymes are in various stages of clinical trials. ANGIOZYME was the first chemically synthesized ribozyme to be studied in human clinical trials. ANGIOZYME specifically inhibits formation of the VEGF-r (Vascular Endothelial Growth Factor receptor), a key component in the angiogenesis pathway. Ribozyme Pharmaceuticals, Inc., as well as other firms have demonstrated the importance of anti-angiogenesis therapeutics in animal models. HEPTAZYME, a ribozyme designed to selectively destroy Hepatitis C Virus (HCV) RNA, was found effective in decreasing Hepatitis C viral RNA in cell culture assays (Ribozyme Pharmaceuticals, Incorporated—http://www.rpi.com/index.html).

An additional method of downregulating H19RNA is via triplex forming oligonucleotides (TFOs). In the last decade, studies have shown that TFOs can be designed which can recognize and bind to polypurine/polypirimidine regions in double-stranded helical DNA in a sequence-specific manner. Thus the DNA sequence encoding the H19 RNA of the present invention can be targeted thereby down-regulating the RNA molecule.

The recognition rules governing TFOs are outlined by Maher III, L. J., et al., Science (1989) 245:725-730; Moser, H. E., et al., Science (1987) 238:645-630; Beal, P. A., et al., Science (1991) 251:1360-1363; Cooney, M., et al., Science (1988) 241:456-459; and Hogan, M. E., et al., EP Publication 375408. Modification of the oligonucleotides, such as the introduction of intercalators and backbone substitutions, and optimization of binding conditions (pH and cation concentration) have aided in overcoming inherent obstacles to TFO activity such as charge repulsion and instability, and it was recently shown that synthetic oligonucleotides can be targeted to specific sequences (for a recent review see Seidman and Glazer (2003) J Clin Invest; 112:487-94).

In general, the triplex-forming oligonucleotide has the sequence correspondence:

| oligo | 3'--A | G | G | T |
|---|---|---|---|---|
| duplex | 5'--A | G | C | T |
| duplex | 3'--T | C | G | A |

However, it has been shown that the A-AT and G-GC triplets have the greatest triple helical stability (Reither and Jeltsch (2002), BMC Biochem, Sept12, Epub). The same authors have demonstrated that TFOs designed according to the A-AT and G-GC rule do not form non-specific triplexes, indicating that the triplex formation is indeed sequence specific.

Thus for any given sequence in the regulatory region a triplex forming sequence may be devised. Triplex-forming oligonucleotides preferably are at least 15, more preferably 25, still more preferably 30 or more nucleotides in length, up to 50 or 100 bp.

Transfection of cells (for example, via cationic liposomes) with TFOs, and subsequent formation of the triple helical structure with the target DNA, induces steric and functional changes, blocking transcription initiation and elongation, allowing the introduction of desired sequence changes in the endogenous DNA and results in the specific downregulation of gene expression. Examples of such suppression of gene expression in cells treated with TFOs include knockout of episomal supFG1 and endogenous HPRT genes in mammalian cells (Vasquez et al., Nucl Acids Res. (1999) 27:1176-81, and Puri, et al., J Biol Chem, (2001) 276:28991-98), and the sequence- and target-specific downregulation of expression of the Ets2 transcription factor, important in prostate cancer etiology (Carbone, et al., Nucl Acid Res. (2003) 31:833-43), and the pro-inflammatory ICAM-1 gene (Besch et al., J Biol Chem, (2002) 277:32473-79). In addition, Vuyisich and Beal have recently shown that sequence specific TFOs can bind to dsRNA, inhibiting activity of dsRNA-dependent enzymes such as RNA-dependent kinases (Vuyisich and Beal, Nuc. Acids Res (2000); 28:2369-74).

Additionally, TFOs designed according to the abovementioned principles can induce directed mutagenesis capable of effecting DNA repair, thus providing both downregulation and upregulation of expression of endogenous genes [Seidman and Glazer, J Clin Invest (2003) 112:487-94]. Detailed description of the design, synthesis and administration of effective TFOs can be found in U.S. Patent Application Nos. 2003 017068 and 2003 0096980 to Froehler et al., and 2002 0128218 and 2002 0123476 to Emanuele et al., and U.S. Pat. No. 5,721,138 to Lawn.

It will be appreciated that nucleic acid agents capable of hybridizing H19 mRNA may down-regulate an activity thereof by preventing H19 mRNA binding to another downstream agent.

As mentioned hereinabove, the nucleic acid agents of the present invention (e.g., an siRNA molecule such as those set forth by SEQ ID NO:1, 2, 3 or 4) can be expressed in cells.

It will be appreciated that the agents of the present invention may be expressed directly in the subject (i.e. in vivo gene therapy) or may be expressed ex vivo in a cell system (autologous or non-autologous) and then administered to the subject.

To express such an agent (i.e., to produce an RNA molecule) in mammalian cells, a nucleic acid sequence encoding the agents of the present invention is preferably ligated into a nucleic acid construct suitable for mammalian cell expression. Such a nucleic acid construct includes a promoter sequence for directing transcription of the polynucleotide sequence in the cell in a constitutive or inducible manner.

Constitutive promoters suitable for use with the present invention are promoter sequences which are active under most environmental conditions and most types of cells such as the cytomegalovirus (CMV) and Rous sarcoma virus (RSV). Inducible promoters suitable for use with the present invention include for example the tetracycline-inducible promoter (Zabala M, et al., Cancer Res. 2004, 64(8): 2799-804).

The nucleic acid construct (also referred to herein as an "expression vector") of the present invention includes additional sequences which render this vector suitable for replication and integration in prokaryotes, eukaryotes, or preferably both (e.g., shuttle vectors). In addition, typical cloning vectors may also contain a transcription and translation initiation sequence, transcription and translation terminator and a polyadenylation signal.

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of the present invention is active in the specific cell population transformed. Examples of cell type-specific and/or tissue-specific promoters include promoters such as albumin that is liver specific [Pinkert et al., (1987) Genes Dev. 1:268-277], lymphoid specific promoters [Calame et al., (1988) Adv. Immunol. 43:235-275]; in particular promoters of T-cell receptors [Winoto et al., (1989) EMBO J. 8:729-733] and immunoglobulins; [Banerji et al. (1983) Cell 33729-740], neuron-specific promoters such as the neurofilament promoter [Byrne et al. (1989) Proc. Natl. Acad. Sci. USA 86:5473-5477], pancreas-specific promoters [Edlunch et al. (1985) Science 230:912-916] or mammary gland-specific promoters such as the milk whey promoter (U.S. Pat. No. 4,873,316 and European Application Publication No. 264, 166).

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for the present invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

Polyadenylation sequences can also be added to the expression vector in order to increase RNA stability [Soreq et al., 1974; J. Mol. Biol. 88: 233-45).

Two distinct sequence elements are required for accurate and efficient polyadenylation: GU or U rich sequences located downstream from the polyadenylation site and a highly conserved sequence of six nucleotides, AAUAAA, located 11-30 nucleotides upstream. Termination and polyadenylation signals that are suitable for the present invention include those derived from SV40.

In addition to the elements already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1 (+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A$^+$, pMTO10/A$^+$, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus *Autographa californica* nucleopolyhedrovirus (AcMNPV) as described in Liang C Y et al., 2004 (Arch Virol. 149: 51-60).

Recombinant viral vectors are useful for in vivo expression of the H19 down-regulating agents of the present invention since they offer advantages such as lateral infection and targeting specificity. Lateral infection is inherent in the life cycle of, for example, retrovirus and is the process by which a single infected cell produces many progeny virions that bud off and infect neighboring cells. The result is that a large area becomes rapidly infected, most of which was not initially infected by the original viral particles. This is in contrast to vertical-type of infection in which the infectious agent spreads only through daughter progeny. Viral vectors can also be produced that are unable to spread laterally. This characteristic can be useful if the desired purpose is to introduce a specified gene into only a localized number of targeted cells.

Various methods can be used to introduce the expression vector of the present invention into cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Currently preferred in vivo nucleic acid transfer techniques include transfection with viral or non-viral constructs, such as adenovirus, lentivirus, Herpes simplex I virus, or adeno-associated virus (AAV) and lipid-based systems. Useful lipids for lipid-mediated transfer of the gene are, for example, DOTMA, DOPE, and DC-Chol [Tonkinson et al., Cancer Investigation, 14(1): 54-65 (1996)]. The most preferred constructs for use in gene therapy are viruses, most preferably adenoviruses, AAV, lentiviruses, or retroviruses. A viral construct such as a retroviral construct includes at least one transcriptional promoter/enhancer or locus-defining element(s), or other elements that control gene expression by other means such as alternate splicing, nuclear RNA export, or post-translational modification of messenger. Such vector constructs also include a packaging signal, long terminal repeats (LTRs) or portions thereof, and positive and negative strand primer binding sites appropriate to the virus used, unless it is already present in the viral construct. Optionally, the construct may also include a signal that directs polyadenylation, as well as one or more restriction sites. By way of example, such constructs will typically include a 5' LTR, a tRNA binding site, a packaging signal, an origin of second-strand DNA synthesis, and a 3' LTR or a portion thereof. Other vectors can be used that are non-viral, such as cationic lipids, polylysine, and dendrimers.

Other than containing the necessary elements for the transcription of the inserted coding sequence, the expression construct of the present invention can also include sequences engineered to enhance stability, production, purification, yield or toxicity of the expressed RNA.

As mentioned above, agents capable of down-regulating H19 mRNA can be used to treat cancer either alone (e.g. siRNAs of the present invention) or in combination with other established or experimental therapeutic regimen for such disorders. The present inventors envisage that agents capable of down-regulating H19 mRNA may act synergistically with additional therapeutic methods or compositions and therefore have the potential to significantly reduce the effective clinical doses of such treatments, thereby reducing the often devastating negative side effects and high cost of the treatment. This may be particularly relevant for treating solid tumors associated with hypoxic regions whereby established chemotherapy and radiotherapy regimens are ineffective.

Agents of the present invention may be administered prior to, concommitedly or following the cancer therapy.

As used herein the phrase "cancer therapy" refers to any treatment which acts to prevent, alleviate or diminish a symptom associated with a cancerous disease.

Therapeutic regimen for treatment of cancer suitable for combination with the agents of the present invention or polynucleotide encoding same include, but are not limited to chemotherapy, radiotherapy, phototherapy and photodynamic therapy, surgery, nutritional therapy, ablative therapy, combined radiotherapy and chemotherapy, brachiotherapy, proton beam therapy, immunotherapy, cellular therapy and photon beam radiosurgical therapy. Another form of therapeutic regimen for treatment of cancer suitable for combination with the agents of the present invention is the administration of nucleotide agents which are capable of regulating genes known to be involved in a cancer-regulating or angiogenesis-regulating pathway.

Anti-cancer drugs (i.e. chemotherapeutic agents) that can be co-administered with the compounds of the invention include, but are not limited to Acivicin; Aclarubicin; Acodazole Hydrochloride; Acronine; Adriamycin; Adozelesin; Aldesleukin; Altretamine; Ambomycin; Ametantrone Acetate; Aminoglutethimide; Amsacrine; Anastrozole; Anthramycin; Asparaginase; Asperlin; Azacitidine; Azetepa; Azotomycin; Batimastat; Benzodepa; Bicalutamide; Bisantrene Hydrochloride; Bisnafide Dimesylate; Bizelesin; Bleomycin Sulfate; Brequinar Sodium; Bropirimine; Busulfan; Cactinomycin; Calusterone; Caracemide; Carbetimer; Carboplatin; Carmustine; Carubicin Hydrochloride; Carzelesin; Cedefingol; Chlorambucil; Cirolemycin; Cisplatin; Cladribine; Crisnatol Mesylate; Cyclophosphamide; Cytarabine; Dacarbazine; Dactinomycin; Daunorubicin Hydrochloride; Decitabine; Dexormaplatin; Dezaguanine; Dezaguanine Mesylate; Diaziquone; Docetaxel; Doxorubicin; Doxorubicin Hydrochloride; Droloxifene; Droloxifene Citrate; Dromostanolone Propionate; Duazomycin; Edatrexate; Eflornithine Hydrochloride; Elsamitrucin; Enloplatin; Enpromate; Epipropidine; Epirubicin Hydrochloride; Erbulozole; Esorubicin Hydrochloride; Estramustine; Estramustine Phosphate Sodium; Etanidazole; Etoposide; Etoposide Phosphate; Etoprine; Fadrozole Hydrochloride; Fazarabine; Fenretinide; Floxuridine; Fludarabine Phosphate; Fluorouracil; Fluorocitabine; Fosquidone; Fostriecin Sodium; Gemcitabine; Gemcitabine Hydrochloride; Hydroxyurea; Idarubicin Hydrochloride; Ifosfamide; Ilmofosine; Interferon Alfa-2a; Interferon Alfa-2b; Interferon Alfa-n1; Interferon Alfa-n3; Interferon Beta-I a; Interferon Gamma-I b; Iproplatin; Irinotecan Hydrochloride; Lanreotide Acetate; Letrozole; Leuprolide Acetate; Liarozole Hydrochloride; Lometrexol Sodium; Lomustine; Losoxantrone Hydrochloride; Masoprocol; Maytansine; Mechlorethamine Hydrochloride; Megestrol Acetate; Melengestrol Acetate; Melphalan; Menogaril; Mercaptopurine; Methotrexate; Methotrexate Sodium; Metoprine; Meturedepa; Mitindomide; Mitocarcin; Mitocromin; Mitogillin; Mitomalcin; Mitomycin; Mitosper; Mitotane; Mitoxantrone Hydrochloride; Mycophenolic Acid; Nocodazole; Nogalamycin; Ormaplatin; Oxisuran; Paclitaxel; Pegaspargase; Peliomycin; Pentamustine; Peplomycin Sulfate; Perfosfamide; Pipobroman; Piposulfan; Piroxantrone Hydrochloride; Plicamycin; Plomestane; Porfimer Sodium; Porfiromycin; Prednimustine; Procarbazine Hydrochloride; Puromycin; Puromycin Hydrochloride; Pyrazofurin; Riboprine; Rogletimide; Safingol; Safingol Hydrochloride; Semustine; Simtrazene; Sparfosate Sodium; Sparsomycin; Spirogermanium Hydrochloride; Spiromustine; Spiroplatin; Streptonigrin; Streptozocin; Sulofenur; Talisomycin; Taxol; Tecogalan Sodium; Tegafur; Teloxantrone Hydrochloride; Temoporfin; Teniposide; Teroxirone; Testolactone; Thiamiprine; Thioguanine; Thiotepa; Tiazofuirin; Tirapazamine; Topotecan Hydrochloride; Toremifene Citrate; Trestolone Acetate; Triciribine Phosphate; Trimetrexate; Trimetrexate Glucuronate; Triptorelin; Tubulozole Hydrochloride; Uracil Mustard; Uredepa; Vapreotide; Verteporfin; Vinblastine Sulfate; Vincristine Sulfate; Vindesine; Vindesine Sulfate; Vinepidine Sulfate; Vinglycinate Sulfate; Vinleurosine Sulfate; Vinorelbine Tartrate; Vinrosidine Sulfate; Vinzolidine Sulfate; Vorozole; Zeniplatin; Zinostatin; Zorubicin Hydrochloride. Additional antineoplastic agents include those disclosed in Chapter 52, Antineoplastic Agents (Paul Calabresi and Bruce A. Chabner), and the introduction thereto, 1202-1263, of Goodman and Gilman's "The Pharmacological Basis of Therapeutics", Eighth Edition, 1990, McGraw-Hill, Inc. (Health Professions Division).

The agents of the present invention may, if desired, be presented in a pack or dispenser device, such as a FDA approved kit, which may contain one or more unit dosage forms containing the agents of the present invention. The agents may be co-formulated in a single packaging with the additional anti cancer agent or the agents may be formulated separately from the additional anti-cancer agent in separate packaging. The pack may, for example, comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising the agents of the invention formulated in a compatible pharmaceutical carrier may also be prepared, placed in an appropriate container, and labeled for the treatment of cancer.

The agents of the present invention can be administered to a subject per se, or in a pharmaceutical composition where it is mixed with suitable carriers or excipients.

As used herein a "pharmaceutical composition" refers to a preparation of one or more of the active ingredients described herein with other chemical components such as physiologically suitable carriers and excipients. The purpose of a pharmaceutical composition is to facilitate administration of a compound to an organism.

Herein the term "active ingredient" refers to the agent accountable for the anti-cancer effect.

Hereinafter, the phrases "physiologically acceptable carrier" and "pharmaceutically acceptable carrier" which may be interchangeably used refer to a carrier or a diluent that does not cause significant irritation to an organism and does not abrogate the biological activity and properties of the administered compound. An adjuvant is included under these phrases.

Herein the term "excipient" refers to an inert substance added to a pharmaceutical composition to further facilitate administration of an active ingredient. Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration may, for example, include oral, rectal, transmucosal, especially transnasal, intestinal or parenteral delivery, including intramuscular, subcutaneous and intramedullary injections as well as intrathecal, direct intraventricular, intravenous, intraperitoneal, intranasal, or intraocular injections.

Alternately, one may administer the pharmaceutical composition in a local rather than systemic manner, for example, via injection of the pharmaceutical composition directly into the tumor (i.e. in situ).

Pharmaceutical compositions of the present invention may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer. For transmucosal administration, penetrants appropriate to the barrier to be permeated are used in the formulation. Such penetrants are generally known in the art.

For oral administration, the pharmaceutical composition can be formulated readily by combining the active compounds with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active compound doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration by nasal inhalation, the active ingredients for use according to the present invention are conveniently delivered in the form of an aerosol spray presentation from a pressurized pack or a nebulizer with the use of a suitable propellant, e.g., dichlorodifluoromethane, trichlorofluoromethane, dichloro-tetrafluoroethane or carbon dioxide. In the case of a pressurized aerosol, the dosage unit may be determined by providing a valve to deliver a metered amount. Capsules and cartridges of, e.g., gelatin for use in a dispenser may be formulated containing a powder mix of the compound and a suitable powder base such as lactose or starch.

The pharmaceutical composition described herein may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

Pharmaceutical compositions for parenteral administration include aqueous solutions of the active preparation in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredient may be in powder form for constitution with a suitable vehicle, e.g., sterile, pyrogen-free water based solution, before use.

The pharmaceutical composition of the present invention may also be formulated in rectal compositions such as suppositories or retention enemas, using, e.g., conventional suppository bases such as cocoa butter or other glycerides.

Pharmaceutical compositions suitable for use in context of the present invention include compositions wherein the active ingredients are contained in an amount effective to achieve the intended purpose. More specifically, a therapeutically effective amount means an amount of active ingredients (nucleic acid construct) effective to prevent, alleviate or ameliorate symptoms of a disorder (e.g., ischemia) or prolong the survival of the subject being treated.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma or brain levels of the active ingredient are sufficient to induce or suppress the biological effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of a composition to be administered will, of course, be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredient. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert. Compositions comprising a preparation of the invention formulated in a compatible pharmaceutical carrier may also be prepared, placed in an appropriate container, and labeled for treatment of an indicated condition, as if further detailed above.

It is expected that during the life of this patent many relevant cancer therapies will be developed and the scope of the term cancer therapy is intended to include all such new technologies a priori.

As used herein the term "about" refers to ±10%.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N.Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987;

3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Detection of an Alternative Splice Variant of H19 in Human Embryonic and Placental Specimens The following experiments were performed in order to ascertain whether splice variants of H19 were restricted to a particular cell type.

Materials and Methods

Cell culture: All the human carcinoma cell lines used in this study were obtained from the American type culture collection (Manassas, Va.) and were maintained in DMEM-F12 (1:1) medium containing 10% fetal calf serum (inactivated 55° C. for 30 minutes), 25 mM HEPES (pH 7.4), penicillin (180 units/ml), streptomycin (100 µg/ml) and amphotericin B (0.2 µg/ml). Approximately $4 \times 10^4$ cells/cm$^2$ were plated in polystyrene culture dishes (NUNC). Every 4 days, the cells were trypsinized with 0.05% trypsin-EDTA solution (Biet Haemek) for 10 minutes and re-plated again at the same initial densities.

Reverse Transcriptase Polymerase Chain Reaction (RT-PCR): Total RNA was extracted from tissues and cultured cell lines using the TRI REAGENT (Sigma) according to the manufacturer's instructions and treated with DNase I to exclude genomic DNA contamination as described previously (Ayesh and Matouk et al, 2002, Mol Ther 7, 535-541). The synthesis of cDNA was performed using the p(dT)15 primer (Roche, Germany), to initiate reverse transcription of 5 µg total RNA with 400 units of Reverse Transcriptase (Gibco BRL), according to manufacturer's instructions. The PCR reaction was carried out in the presence of Diaza dGTP (Roche, Germany) with Taq polymerase (Takara, Otsu, Japan) for 40 cycles (94° C. for 1 min, 58° C. for 30 s, and 72° C. for 40 s) preceded by 94° C. for 5 min, and a final extension of 5 min at 72° C. The primers used in the PCR reaction were (5'-AGGAGCACCTTGGACATCTG-3') (SEQ ID NO: 8) and (5'-CCCCTGTGCCTGCTACTAAA-3') (SEQ ID NO: 9) and were 117 and 816 bases downstream to the published transcription H19 initiation site, respectively (Brannan et al, 1990, Mol Cell Biol 10, 28-36). The position of the primers is illustrated in FIG. 1A. The products of the PCR reaction were run on ethidium bromide stained gels.

Probe Synthesis: PCR products from tissues demonstrating the minor band were purified from the gel by the GFX™ PCR, DNA and Gel Band Purification Kit, and cloned into a T-easy® vector (Promega, USA). The orientation of the insert was verified by restriction enzyme analysis, and accordingly the labeled antisense strand was synthesized using Digoxigenin UTP, according to the supplier's instructions (Roche, Germany). The resulting probe was treated with 2 units of RNase free DNase I, pelleted and resuspended in an appropriate volume of DEPC-treated double distilled water. The size of the synthesized probe was analyzed by running on a 4% denaturing agarose minigel, and its labeling efficiency was determined by dot blot analysis using Digoxigenin antibody (data not shown).

RNase Protection Assay: Various concentrations of third trimester placenta RNA (which showed the presence of the alternative splice variant using the RT-PCR assay) were used in an RNase protection assay. 600 pg Dig-labeled probe/10 µg total RNA (DNase I treated) from third trimester placenta and yeast RNA equals to the highest concentration of RNA used were hybridized at 42° C. for 16 hours and digested with RNase A/and RNase TI, according to the kit instructions RPA II™ (Ambion). The RNA fragments protected from RNase digestion were separated by electrophoresis on a 5% polyacrylamide gel (containing 8 M urea) and were detected using the CDP Star Detection Kit (Roche, Germany), according to the manufacturer's instructions.

DNA Sequencing: Sequencing reactions were carried out using the ABI PRISM BigDye Terminator Cycle Sequencing Ready Reaction Kit (PE Applied Biosystem).

Results

An alternatively spliced variant of H19 was present in placental and embryonic tissues and not in carcinoma cell lines, and cancer patient specimens as demonstrated by RT-PCR analysis (FIGS. 1B-D) and RNase protection assay (FIG. 1E). Sequencing studies showed that the alternative spliced variant was 344 bp long and lacked part of exon-1 extending from nt 252 to 588 of the transcription start site (FIG. 1F) as compared to the known H19 transcript (GenBank Accession No. M32053).

Example 2

H19 Gene Expression is Moderately Up-Regulated by $CoCl_2$

Several genes up regulated in the presence of H19 RNA are also known to be induced by hypoxia (Ayesh and Matouk et al, 2002, Mol Carcinog 35, 63-74). It was also reported that H19 RNA has been detected in rheumatoid arthritis synovial tissue (Stuhlmuller et al, 2003, Am J Pathol 163, 901-911). The presence of extensive angiogenesis is usually associated with rheumatoid arthritis due to hypoxic and oxidative stress, partly due to the metabolic activity of increased inflammatory cell exudates in the affected area.

Moreover, a proteomic approach has revealed that H19 over-expression in human cancerous mammary epithelial cells stably transfected with genomic DNA containing the entire H19 gene, is responsible for positively regulating the thioredoxin gene at post-transcriptional level, thioredoxin being a key protein of the oxidative stress response and deoxynucleotide biosynthesis (Lottin et al, 2002, Carcinogesis 23, 1885-1895).

In addition, many processes that involve cellular invasion, including blastocyst implantation, and placental development occur in reduced oxygen environments (Rodesch et al, 1992, Obstet Gynecol 80, 283-285). These two physiological processes show intensive up regulation of H19 expression (Ariel et al, 1994, Gynecol Oncol 53, 212-219).

Based on those reasoning, the H19 gene was analyzed to determine if it was sensitive to hypoxia.

Materials and Methods

Hep3B cells were cultured in normal medium conditions for 24 hours prior to CoCl$_2$ manipulation. The cells were incubated with CoCl$_2$ (Sigma, Aldrich) for a further 22 hours prior to RNA extraction.

RT-PCR analysis was performed as described above in Example 1 using the following primers 5'-CCG GCC TTC CTG AAC A-3' Forward (SEQ ID NO: 10) and 5'-TTC CGA TGG TGT CTT TGA TGT-3' Reverse (SEQ ID NO: 11)

Results

H19 gene expression is moderately upregulated in Hep3B cells (FIGS. 2A-B) in response to the addition of increasing concentrations of CoCl$_2$ (50-400 uM) as tested by RT-PCR analysis. This moderate up-regulation relative to the strong up-regulation towards real hypoxic conditions indicate that HIF-α is only partly responsible.

Example 3

H19 RNA is Efficiently Down-Regulated In Vitro by Different siRNA Duplexes in Both Normal and Hypoxia-Like Culture Conditions Materials and Methods siRNAs preparation: Four siRNAs targeting human H19 and one negative control siRNA (targeting luciferase pGL3) (as set forth in Table 1 hereinbelow) were synthesized as a ready to use duplexes by Proligo and designed as recommended with dTdT 3' overhangs on each strand. All sequences were evaluated for gene specificity using the National Institutes of Health Blast program.

TABLE 1

| siRNA name | Sense sequence | Location | SEQ ID NO: |
|---|---|---|---|
| H19 siRNA-1 | 5'-UAAGUCAUUUGCACUGGUUdTdT-3' | Exon 5 | 1 |
| H19 siRNA-2 | 5'-GCAGGACAUGACAUGGUCCdTdT-3' | Exon 2 | 2 |
| H19 siRNA-3 | 5'-CCAACAUCAAAGACACCAUdTdT-3' | Exon 5 | 3 |
| H19 siRNA-4 | 5'-CCAGGCAGAAAGAGCAAGAdTdT-3' | Exon 1 | 4 |
| PG13 siRNA | 5'-CUUACGCUGAGUACUUCGAdTdT-3' | Exon 1 | 5 |
| GFP siRNA | 5'- GCA AGC UGA CCC UGA AGU UCA U | | 6 |

Upon receiving each freeze dried siRNA was reconstituted with RNase free water to prepare a 50 pmole/ul solution and stored as aliquots at −80° C.

Cell culture conditions and transfection of siRNAs: Transfection of siRNAs was conducted with lipofectamine 2000 (Invitrogen, US) in 12-well plates. The day prior to transfection, the cells were trypsinized, counted, and seeded at 60,000/well containing 1 ml DMEM medium without antibiotics so that they were nearly 50% confluent on the day of transfection. 3 µl of lipofectamine 2000 was incubated for 15 minutes with 100 µl serum-free OPTI-MEM medium, (Invitrogen, US). This was added to the 100 pmole dsRNA diluted in 100 µl serum free OPTI-MEM media and the formulation lasted 20 minutes. 195 µl of the mixture was applied to Hep3B cells and UMUC3 cells and incubated for another 48 hours without replacement of the medium. For hypoxia mimicking conditions freshly prepared CoCl$_2$ was added at a final concentration of 100 µM 24 hours post transfection and the cells were incubated for a further 22 hours prior to RNA extraction.

RNA extraction and RT-PCR conditions (siRNA): Total RNA and reverse transcription was performed as described above in Example 1 except that 1 µg of total RNA was used. The PCR reaction for H19 was carried out in the presence of Taq polymerase (Takara, Otsu, Japan) for 34 cycles (94° C. for 30 s, 58° C. for 30 s, and 72° C. for 30 s) preceded by 94° C. for 5 min, and a final extension of 5 min at 72° C., and for GADPH and histone. Primer sequences for GAP: forward 5'-GGC TCT CCA GAA CAT CAT CCC TGC-3' (SEQ ID NO: 12) and Reverse GGG TGT CGC TGT TGA AGT CAG AGG-3' (SEQ ID NO: 13).

Results

Hep3B cells: The ability of siRNA to reduce the endogenous level of H19 RNA under both normal (FIG. 3A), or hypoxia like conditions (FIG. 3B) was examined. Dramatic suppression of H19 expression was detected by RT-PCR analysis (48 hours post transfection) using four different siRNAs (1-4) targeting H19 (FIG. 3A, lanes 2-5) or the equimolar pool of the four siRNA (FIG. 3A, lane 6) but not with non-related PGl3 duplex targeting luciferase (FIG. 3A, lane 1) and mock (FIG. 3A, lane 7) respectively. Moreover, the ability of three different siRNA (1, 3 and 4) to suppress the expression of H19 gene was tested in hypoxia-like CoCl$_2$ simulation (FIGS. 3B-C). While H19 RNA is moderately induced by CoCl$_2$ simulation (compare FIG. 3B lanes 1 for hypoxic simulation and 5 for normal both transfected with PGl3 duplexes), dramatic reduction was detected using three different siRNA targeting H19 transcript (FIG. 3B, lanes 2-4).

UMUC3 cells: As with Hep3B cells, hypoxic conditions increased the expression of H19 message and the siRNA H19 (SEQ ID NO: 1) very significantly reduced its expression (FIGS. 3D-E).

Example 4

Ex-Vivo Down-Regulation of H19 RNA in Both Hep3B and UMUC3 Cells Reduces In Vivo Tumorigenicity Materials and Methods Ex-vivo tumorigenic assay: Hep3B and UMUC3 cells were transfected in vitro by two different siRNA duplexes directed against H19 RNA (siRNA SEQ ID NO: 3 for Hep3B cells and siRNA SEQ ID NO: 1 for UMUC3) and an unrelated control siRNA (targeting Luc or GFP), respectively as described above. Forty eight hours post transfection, cells were injected subcutaneously into the dorsal flank region of athymic nude mice. An additional control group was without any treatment. Cells were trypsinized, counted, and centrifuged and re-suspended into sterile PBS (1×), so that there were about 5×10$^6$ cells/ml. 250 µl of the suspension was injected into the dorsal flank region of athymic nude mice. Fifteen and 30 days post injection, tumors begin to develop and their volumes were measured using a caliper.

Transfection of siRNAs was conducted with lipofectamine 2000 (Invitrogen, US) in 6-wells plates. The day prior to transfection, the cells were trypsinized, counted, and seeded at 100,000/well containing 2 ml DMEM medium without antibiotics so that they were nearly 50% confluent on the day of transfection. 5 μl of lipofectamine 2000 incubated for 15 minutes with 250 μl serum-free OPTI-MEM medium (Invitrogen, US). This was added to the 100 uM dsRNA diluted in 250 μl serum free OPTI-MEM media and the formulation lasted 20 minutes. 500 μl of the mixture was applied to the cells and incubated for another 48 hours without replacement of the medium. Each treatment group comprised seven mice.

Results

As illustrated in FIGS. 4A-D, administration of Hep3B cells previously transfected with H19 siRNA to mice caused a very significant lowering in tumor weight (FIG. 4A) and volume (FIG. 4B) than Hep3B cells transfected with Luc siRNA. As illustrated in FIGS. 5A-D, UMUC3 cells transfected with H19 siRNA also caused a very significant lowering in tumor weight (FIG. 5A) and volume (FIG. 5B) in mice than UMUC3 cells transfected with Luc siRNA.

Example 5

Oncogenic Properties of H19 siRNA

In order to ascertain whether H19 RNA is a tumor-associated gene product or whether it is potentially harboring an oncogenic potential by itself, the following experiment was performed.

Materials and Methods

Cell proliferation analysis: Hep3B cells were seeded and transfected in 12 well plates with anti-Luc siRNA or H19 siRNA (SEQ ID NO: 3). Twenty four hours later, cells were washed twice with PBS, trypsinized and counted. $5\times10^3$ transfected Hep3B cells were seeded in quadruples in 96 well plates in DMEM media containing 10% FCS, and further incubated for 24 hours before the MTS assay was performed. MTS assay was performed according to the procedure provided by the supplier (Promega, USA). The absorbance at 940 nm was recorded using ELISA plate reader.

Results

Figure 6:
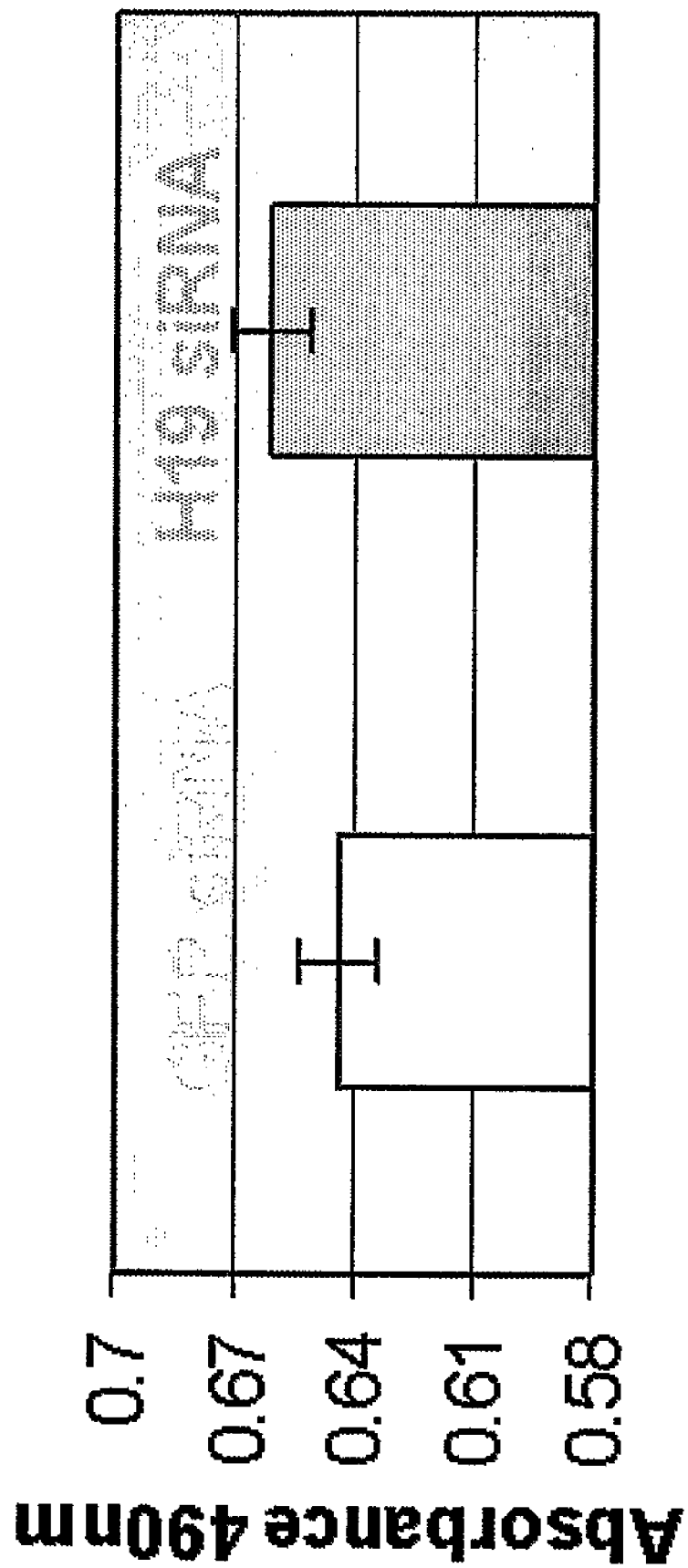
FIG. 6 is a bar graph illustrating the effect of H19 siRNA (SEQ ID NO: 3) transfection in Hep3B cells on proliferation under normal culture conditions.

As shown in FIG. 6, siRNA H19 did not induce a statistically significant attenuation of cell proliferation of Hep3B cells.

Moreover the effect of H19 suppression on anchorage independent colony formation in soft agar after hypoxia recovery was also analyzed as an additional assessment of tumorigenicity in vitro. Hep3B cells were exposed to hypoxic stress 4 hours post transfection as described in the materials and methods. 24 hours post hypoxic conditions, cells were seeded on soft agar. H19 siRNA significantly abrogated anchorage independent growth after hypoxia recovery in which both colony number and size were very significantly reduced (FIG. 3F).

Example 6

In-Vivo Intra-Tumoral Injection of H19 siRNA Duplex

Materials and Methods

Preparation of H19siRNAs: The transfectant used was jet-PEI™ (×4) conc from Polyplus. 850 pmoles (~11 μg of siRNAs), and 10 μl of jetPEI (N/P=10), were diluted in 100 μl 5% glucose solution, 5 minutes after, jetPEI solution was added to siRNAs solutions and the formulation lasted 20 minutes before intratumoral (for UMUC3) or initial inoculation site (for Hep3B) injections.

Experimental procedure: $2\times10^6$ bladder carcinoma cells (UMUC3), and hepatocellular carcinoma (Hep3B) cells were suspended in 100 μl PBS and injected subcutaneously in the dorsa of 10 athymic male mice, for UMUC3 and 8 for Hep3B.

UMUC3 cells: When the tumors reach about 4-8 mm in diameter in UMUC3, mice were segregated to two homogeneous groups (n=5), and received the first intratumoral siRNA injection of unrelated GFP as a control or H19 siRNAs (H19 siRNA-3—SEQ ID NO: 3). A total of 3 injections were administered at 2 and 5 days intervals following the first intratumoral injection and mice were left 6 days post final injection without any treatment. Tumor volumes for the two treated groups were measured using a caliper, and their final tumor weights were recorded.

Hep3B cells: For Hep3B cells, treatment followed 48 hours following cell inoculation before palpable tumors were observed. The mice were segregated into two groups (n=4 each), and injected at the site of initial inoculation. Mice received a total of 5 injections, every two days, and then left for a week post final injection before scarifying them.

Tumor volume was calculated by the equation, $V=(L\times W^2)\times 0.5$ (V, volume; L, length; and W, width).

Results

Figure 7A:
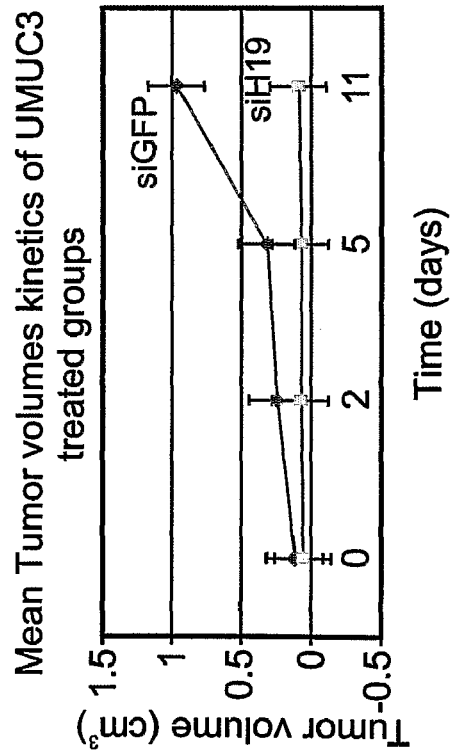
Figure 7C:
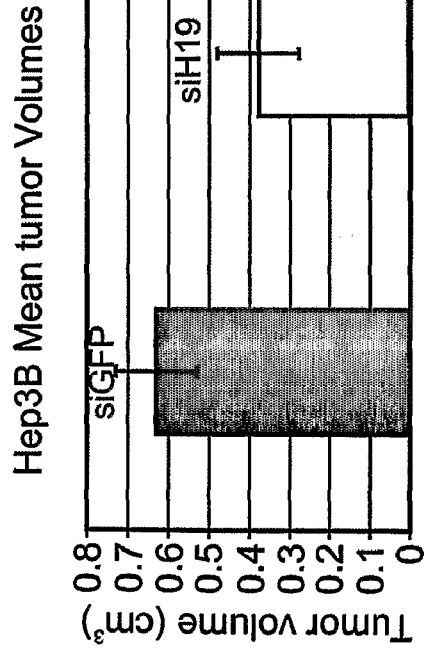

To determine the functional consequences of H19 knockdown in tumor growth, H19 siRNA-PEI complex was injected into small tumors induced from bladder carcinoma UMUC3 cell line and before palpable tumors were observed in Hep3B carcinoma cell line in nude mice. Synthetic control siRNA targeting GFP formulated with PEI was used as a control. As shown in FIGS. 7A-B, H19 siRNA3 causes a very significant reduction of about 90% of mean tumor volumes (FIG. 7A), and of about 88% of mean tumor weights (FIG. 7B) in UMUC3 cells.

In Hep3B induced tumors, the level of reduction in tumor volumes and weights are less pronounced using siRNA1. An approximate 40% reduction of tumor weights (FIG. 7C) and 56% reduction of tumor volumes (FIG. 7D) were observed.

Example 7

H19 Involvement in TA11 and TA31 Cells

Two human bladder carcinoma cells lines, TA11 and TA31, originating from the same parental cell line T24P were shown to be either negative, (TA11H19-ve) or to be high expressers (TA31H19high) of H19 in vitro under normal culture conditions, respectively [Ayesh et al, 2002, Mol Carcinog 35, 63-74]. The following experiment was performed in order to determine whether the H19 message effects tumor growth of these other cell lineages.

Materials and Methods

TA11 and TA31 cells (approximately $2\times10^6$) were implanted subcutaneously into CD-1 mice (n=5 each). Tumor volumes were measured 15 days post-implantation. As shown in FIGS. 8A-B, tumors derived from the TA11H19-ve cells were significantly smaller than those from the TA31H19high cells. Furthermore, the TA31H19high-derived tumors were significantly more vascularized (FIGS. 8C-D). RT-PCR results from the tumors that obtained from TA11H19-ve cells show that H19 RNA is induced in those tumors as opposed to null expression of H19 RNA in those cells in vitro (data not shown). These results suggest that H19 RNA enhances tumor growth.

Example 8

H19 RNA is Induced by Hypoxic Stress in Hep3B Cell Line and siRNA Directed Against H19 Very Efficiently Impedes its Induction

Materials and Methods

Hep3B cells were seeded and transfected either with anti H19 siRNA or anti Luc siRNA as described above. 24 hours post transfection, cells were either placed into Aneoropack rectangular jar (Mitsubishi chemical company Japan) to create a hypoxic conditions within an hour (1% $O_2$, 20% $CO_2$), or left in normal oxygen concentrations. Incubation lasted for 24 hours prior to RNA extraction. RT-PCR analysis was performed as described for Example 1 hereinabove.

Results

As illustrated in FIG. 9A, H19 RNA was specifically down-regulated both in normal (FIG. 9A, lane 3) and hypoxic (FIG. 9A, lane 4) culture conditions respectively. PCR analysis of house-keeping genes (GAPDH) is illustrated in FIG. 9B. PCR analysis of uPAR is illustrated in FIG. 9C.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. An isolated oligonucleotide able to down-regulate H19 mRNA under both normal and hypoxic conditions as set forth in SEQ ID NO: 1.

2. A pharmaceutical composition comprising a pharmaceutically acceptable carrier and, as an active ingredient, at least one isolated oligonucleotide according to claim 1.

3. An article of manufacture identified for treating cancer comprising an agent capable of downregulating a level and/or activity of H19 mRNA, wherein said agent is an siRNA able to down-regulate H19 mRNA under both normal and hypoxic conditions which comprises a nucleic acid sequence selected from the group consisting of as set forth in SEQ ID NO: 1, and an additional anti cancer agent.

4. The article of manufacture of claim 3, wherein said cancer is a bladder carcinoma or a hepatocellular carcinoma.

5. The article of manufacture of claim 3, wherein said agent capable of downregulating a level and/or activity of H19 mRNA is co-formulated with said additional anti cancer agent.

6. A nucleic acid construct encoding the oligonucleotide of claim 1.

* * * * *

UNITED STATES PATENT AND TRADEMARK OFFICE
CERTIFICATE OF CORRECTION

| | | |
|---|---|---|
| PATENT NO. | : 8,067,573 B2 | |
| APPLICATION NO. | : 11/994810 | |
| DATED | : November 29, 2011 | |
| INVENTOR(S) | : Hochberg et al. | |

It is certified that error appears in the above-identified patent and that said Letters Patent is hereby corrected as shown below:

Column 37:
Line 19, delete "selected"

Column 38:
Line 8, delete "from the group consisting of".

Signed and Sealed this
Third Day of January, 2012

David J. Kappos
*Director of the United States Patent and Trademark Office*